United States Patent
Maaβ et al.

(10) Patent No.: US 9,855,207 B2
(45) Date of Patent: *Jan. 2, 2018

(54) UV-PHOTO-PROTECTING COSMETIC COMPOSITION

(75) Inventors: Sebastian Maaβ, Elsdorf (DE); Roland Wagner, Bonn (DE); Karl-Heinz Sockel, Leverkusen (DE); Mark Davis, Köln (DE); Albert Schnering, Köln (DE); Katharina Streicher, Leverkusen (DE)

(73) Assignee: Momentive Performance Materials GmbH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/979,411

(22) PCT Filed: Jan. 26, 2012

(86) PCT No.: PCT/EP2012/051204

§ 371 (c)(1),
(2), (4) Date: Aug. 28, 2013

(87) PCT Pub. No.: WO2012/101204

PCT Pub. Date: Aug. 2, 2012

(65) Prior Publication Data

US 2013/0330385 A1 Dec. 12, 2013

(30) Foreign Application Priority Data

Jan. 28, 2011 (EP) .................... 11152490

(51) Int. Cl.
*A61K 8/89* (2006.01)
*A61K 8/02* (2006.01)
*A61K 8/49* (2006.01)
*A61K 8/893* (2006.01)
*A61K 8/898* (2006.01)
*A61Q 17/04* (2006.01)
*C08G 77/388* (2006.01)
*C08G 77/14* (2006.01)

(52) U.S. Cl.
CPC ............... *A61K 8/89* (2013.01); *A61K 8/02* (2013.01); *A61K 8/4966* (2013.01); *A61K 8/893* (2013.01); *A61K 8/898* (2013.01); *A61Q 17/04* (2013.01); *C08G 77/388* (2013.01); *A61K 2800/412* (2013.01); *C08G 77/14* (2013.01)

(58) Field of Classification Search
None
See application file for complete search history.

(56) References Cited

U.S. PATENT DOCUMENTS

| | | | |
|---|---|---|---|
| 6,403,061 B1 | 6/2002 | Candau et al. | |
| 2001/0018044 A1 | 8/2001 | Nakanishi et al. | |
| 2007/0098653 A1 | 5/2007 | Tamasawa et al. | |
| 2007/0184006 A1* | 8/2007 | Ferenz et al. | 424/70.12 |
| 2008/0199417 A1* | 8/2008 | Joffre et al. | 424/70.12 |
| 2010/0266651 A1* | 10/2010 | Czech et al. | 424/401 |
| 2010/0303746 A1 | 12/2010 | Mongiat et al. | |

OTHER PUBLICATIONS

Goddard et al. Eds., Principles of Polymer Science and Technology in Cosmetics and Personal Care, CRC Press 1999, Chapter 7, pp. 1-50.*
Evonik, Emulsifiers for skin care application, 2008, pp. 1-20.*
International Search Report for corresponding PCT/EP2012/051204 dated Jun. 19, 2012, three pages.
International Preliminary Report on Patentability for corresponding PCT/EP2012/051204 dated Aug. 8, 2013, seven pages.

* cited by examiner

*Primary Examiner* — Bethany P Barham
*Assistant Examiner* — Ping Cao
(74) *Attorney, Agent, or Firm* — Rankin, Hill & Clark LLP

(57) ABSTRACT

The present invention relates to an UV-photo-protecting cosmetic composition, including:
(a) at least one aqueous phase,
(b) at least one fatty phase,
(c) at least one micronized organic UV-screening agent, the mean particle size of said micronized particles ranging from 0.01 to 2 μm, and
(d) at least one organomodified silicone which does not include poly(oxyalkylene) moieties.

17 Claims, No Drawings

UV-PHOTO-PROTECTING COSMETIC COMPOSITION

The present invention relates to a UV-photo-protecting cosmetic composition comprising a specific organomodified silicone which does not comprise poly(oxyalkylene) moieties. In particular, the present invention relates to novel emulsions comprising at least one aqueous phase and at least one fatty phase; at least one organic UV-screening agent insoluble in such emulsions, in micronized form or state; and also including at least one organomodified silicone free of poly(oxyalkylene) moieties.

DESCRIPTION OF THE PRIOR ART

It is known that light radiation of wavelengths of from 280 nm to 400 nm permits tanning of the human epidermis, and that radiation of wavelengths more particularly of from 280 nm to 320 nm, UV-B radiation, causes erythemas and skin burns which can hinder the development of natural tanning. For these reasons as well as for aesthetic reasons, there is a constant demand to control this natural tanning such as to thereby control the color of the skin; it is therefore advisable to screen out UV-B radiation.

It is also known to this art that UV-A radiation of wavelengths of from 320 nm to 400 nm, which promotes tanning of the skin, also is capable of causing damage thereto, in particular in the case of a sensitive skin or of a skin continually exposed to solar radiation. UV-A radiation, causes, in particular, loss of elasticity of the skin and the appearance of wrinkles which promotes premature skin aging. UV-A radiation promotes the onset of the erythema reaction or amplifies this reaction in certain individuals and may even be responsible for phototoxic or photoallergic reactions. Thus, for aesthetic and cosmetic reasons such as the preservation of the natural elasticity of the skin for example, an increasing number of individuals seek to control the effect of UV-A radiation on their skin. It is therefore desirable to also screen out UV-A radiation.

A wide variety of cosmetic compositions intended for the photoprotection (UV-A and/or UV-B) of the skin are also known to this art.

These anti-sun or sunscreen compositions are quite often provided in the form of an emulsion, of the oil-in-water (O/W) type (namely, a cosmetically and/or dermatologically acceptable carrier comprising an aqueous dispersing continuous phase and a fatty dispersed discontinuous phase) or of the water-in-oil (W/O) type (dispersed aqueous phase in a continuous fatty phase), which contains, at various concentrations, one or more lipophilic conventional organic UV-screening agents and/or inorganic nanopigments of metal oxides, which are suited for selectively absorbing the harmful UV radiation, these screening agents (and the quantities thereof) being selected according to the desired sun protection factor (the sun protection factor (SPF) being mathematically expressed by the ratio of the irradiation time required to attain the erythematogenic threshold with the UV-screening agent to the time required to attain the erythematogenic threshold in the absence of UV-screening agent). The oil-in-water emulsions are, in general, more accepted by the consumer than the water-in-oil emulsions because, in particular, of their pleasant feel (similar to water) and their presentation in the form of a non-oily cream or milk; however, they also more readily lose their UV protection efficacy as soon as they come into contact with water. Indeed, the hydrophilic screening agents tend to disappear in water, upon washing in the sea or in a swimming pool, under the shower or when engaged in water sports; thus, anti-sun or sunscreen compositions containing same, whether alone or combined with lipophilic screening agents, no longer provide the desired initial protection as soon as the substrate (skin or hair) to which they have been applied is contacted with water. Anti-sun (sunscreen) compositions exhibiting improved resistance to water have been formulated as water-in-oil emulsions. Indeed, a hydrophilic screening agent is more stable to water in a water-in-oil emulsion than in an oil-in-water emulsion. However, as indicated above, such compositions are not yet completely satisfactory since they promote, after application, a fat-like impression which is particularly unpleasant for the user.

U.S. Pat. No. 6,403,061 describes UV photo-protecting W/O emulsions. Certain poly(oxyalkylated) silicones are used as W/O emulsifiers to stabilize the formulations. Disadvantage is that these poly(oxyalkylated) silicones itself and/or low molecular weight poly(oxyalkylated) monomer traces and/or by products are suspected to have potentially a skin sensitizing effect.

Recently, amodimethicone glycerocarbamates were presented as W/O alkylene oxide free emulsifiers (COSSMA 7-8 2010, p.18).

The cohydrosilylation of SiH functionalized siloxanes with C=C unsaturated oligoglycerols and long chained alkenes yields alkylene oxide free W/O emulsifiers (SÖFW-Journal, 132, 12-2006, 31; US 2010/0266651).

The cohydrosilylation of SiH functionalized siloxanes with C=C unsaturated oligo glycerols and in the alcohol part C=C unsaturated fatty acid esters yields another type of alkylene oxide free W/O emulsifiers (US 2009/0062459). The document does not disclose any specific sunscreen composition.

One of the most serious problems in sunscreen compositions is the provision of an emulgator that provides stability to aqueous emulsions comprising large amounts of organic water-insoluble UV-screening agents, in particular those of the triazine-type. Thus there has been a strong desire to find specific emulgators that can provide stable emulsions for these types of organic water-insoluble UV-screening agents, in particular at high loading levels of these organic water-insoluble UV-screening agents.

Further serious need exists for anti-sun or sunscreen compositions which impart to the skin and/or the hair effective solar protection which is stable over time and resistant to water (stability to water) and a cosmetic performance which is comparable to the one obtained with state of the art poly(oxyalkylated) silicones without having the above mentioned disadvantages of these poly(oxyalkylated) silicones.

SUMMARY OF THE INVENTION

It has now surprisingly and unexpectedly been determined that particular organomodified silicones free of poly(oxyalkylene) moieties can be used to overcome the above mentioned disadvantages. These emulsions provide cosmetic performance features comparable to those generally associated with advanced water/oil emulsions based on poly(oxyalkylated) silicones, and at the same time allow for high loadings of in particular triazine-based UV sunscreen agents without affecting stability of the emulsions. Also the organomodified silicones free of poly(oxyalkylene) moieties provide high stability of the fatty film, comprising the UV sunscreen agents deposited on the skin.

Thus the present invention provides UV-photo-protecting cosmetic compositions, comprising:
a) at least one aqueous phase,
b) at least one fatty phase,
c) at least one micronized organic UV-screening agent, the mean particle size of said micronized particles ranging from 0.01 to 2 μm, and
d) at least one organomodified silicone which does not comprise poly(oxyalkylene) moieties.

According to the present invention, cosmetic compositions include all kind of cosmetic or dermatological emulsions in which the aqueous phase and the fatty phase contain substances or substrates which are cosmetically or dermatologically acceptable for topical application onto human keratinous materials including the skin, the hair, the eyelashes, the eyebrows, the lips, the nails or the mucous membranes.

The at least one micronized organic UV-screening agent, the mean particle size of said micronized particles ranging from 0.01 to 2 μm, are preferably water-insoluble organic UV-screening agents which are insoluble in the cosmetic compositions. Generally included in the cosmetic anti-sun formulations of the invention are particularly those whose solubility in water at 25° C. is less than 0.1% by weight and/or those whose solubility in paraffin oil at 25° C. is less than 1% by weight.

The term "mean particle size" used in accordance with the present invention refers to the volume average particle size as determined with a Beckman Coulter Particle Sizer Model LS 13320 calculated preferably according to the Mie-Theory of light scattering applying the method ISO 13320-1 (1990): Particle size analysis—Laser diffraction methods. (See also I. Zimmermann Ingenieur Technik 68 (1996) Nr. 4). The term "photo-protective cosmetic composition" include any composition screening out UV-A and/or UV-B radiation.

The present invention also provides a method of formulating the subject cosmetic compositions, in particular, formulating organomodified silicones free of poly(oxyalkylene) moieties into photo-protective cosmetic/dermatological emulsions containing at least one organic UV-screening agent preferably insoluble in the emulsion, in micronized form or state, the mean particle size of which ranges from 0.01 to 2 μm, in particular, to increase or enhance the water resistance of the fatty phase that adheres on the skin to maintain their screening power (stability to water). The organomodified silicones free of poly(oxyalkylene) moieties according to the invention may be provided in the form of oils, waxes, resins or gums. They may be water-soluble or insoluble in water.

By "organomodified silicone free of poly(oxyalkylene) moieties" is intended any silicone not containing in its structure a functional group which is based on poly(oxyalkylene) moieties, i.e. those based on at least two ethylene oxide, 1,2 propylene oxide, 1,3 propylene oxide, 1,2 butylene oxide, 1,4 butylene oxide, or 1,2 hexylene oxide moieties. The term "poly(oxyalkylene) moieties" however does not include poly(hydroxyalkyleneoxy) moieties as those derived e.g. from glycerol.

Preferably the organomodified silicone are those of the following structural formula (I):

$$[M_aD_bT_cQ_d]_e \qquad (I)$$

wherein
$M=R_3SiO_{1/2}$,
$D=R_2SiO_{2/2}$,
$T=RSiO_{3/2}$,
$Q=SiO_{4/2}$, with
a=1-10
b=0-1000
c=0-1
d=0-1
e=1-10 wherein R=$C_1$ to $C_{22}$-alkyl, fluoro-substituted $C_1$ to $C_{22}$-alkyl or $C_6$ to $C_{20}$ aryl, which is bound to Si via a carbon atom, with the requirement that at least one group R is replaced by $R^1$, which is selected from:

$R^1$=—Z-(E)$_y$, wherein

Z=a bivalent or trivalent straight-chained, cyclic or branched, saturated or unsaturated $C_2$ to $C_{20}$-hydrocarbon residue, which optionally comprise one or more groups selected from —O—, —NH—,

and which is substituted by one or more OH groups, or a bivalent or trivalent straight-chained, cyclic or branched, saturated or unsaturated $C_2$ to $C_{20}$-hydrocarbon residue (the residue Z being bound to silicon atom via a carbon atom), y=1 or 2
E is selected from the group which comprises:

$E^1$=—O—C(O)—$R^2$, wherein $R^2$=is a straight-chained, cyclic or branched, saturated or unsaturated hydrocarbon residue with up to 50 carbon atoms, which can comprise one or more groups selected from —O—, —NH—, —$NR^3$—, —C(O)— and may be substituted by one or more OH groups, wherein $R^3$=a straight-chained, cyclic or branched, saturated or unsaturated hydrocarbon residue with up to 6 carbon atoms, and $E^2$=—$NR^4R^5$, wherein $R^4$ and $R^5$ are the same or different and are selected from the group which comprises: hydrogen and straight-chained, cyclic or branched, saturated or unsaturated hydrocarbon residue with up to 30 carbon atoms, which can comprise one or more groups selected from —O—, —NH—, —$NR^3$—, wherein $R^3$ is as defined above, —C(O)—, and can be substituted by one or more OH— and/or $H_2N$— groups, $E^3$=—NH—CO(O)—$R^2$, wherein $R^2$ is a defined above.

Preferably the group Z comprises at least one residue which is selected from the group which consists of the formulas:

—(CH$_2$)$_z$— wherein z is 1 to 10,

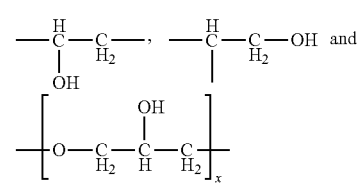

wherein x=1-4.

Still more preferably the group Z is a residue selected from the group of the formulas:

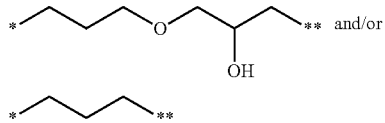 and/or wherein each * denotes the bond to the silicon atom and ** denotes the bond to the residue E.

Preferably the organomodified silicone (d) comprises structural elements selected from the following formulas:

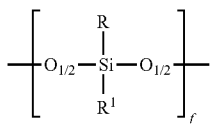

wherein R and $R^1$ are each as defined above, and f=0-600,

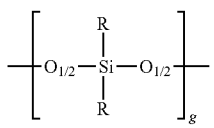

wherein R is as defined above, and g=0-700,

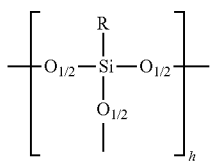

wherein R is as defined above, and h=0-10,

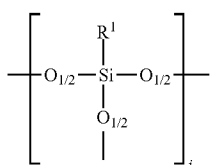

wherein $R^1$ is as defined above, and i=0-10,

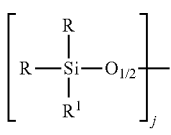

wherein R and $R^1$ are as defined above, and j=0-30,

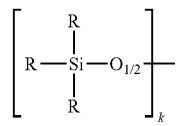

wherein R is as defined above, and k=0-30,

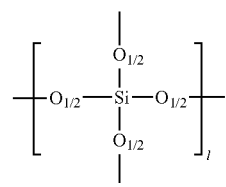

wherein l=0-10, and wherein f+g+h+i+j+k+l=12 to 1000, preferably 20 to 300, still more preferably 30 to 200.

In a further preferred embodiment the organomodified silicone (d) comprises two or more different residues $R^1$, which differ in their hydrophilic characteristics, more preferably the organomodified silicone (d) comprises hydrophilic residues $R^{11}$ and lipophilic residues $R^{12}$. The hydrophilic/lipophilic properties of the residues $R^1$ are essentially controlled by the contribution of polar and non-polar moieties in such residues. For example the longer the alkyl chains in such residues are the more lipophilic they are, and the lager the number of polar groups like hydroxy groups is the more hydrophilic the residues $R^1$ are.

Preferably the hydrophilic residues $R^{11}$ have a logP (25° C.) of <0.5 and the lipophilic residues $R^{12}$ have a logP (25° C.) of ≥0.5, determined on the basis of the corresponding compounds H—$R^{11}$ and H—$R^{12}$, wherein logP (25° C.) represents the partition coefficient of the corresponding compounds H—$R^{11}$ and H—$R^{12}$ in a water-n-octanol mixture at 25° C. According to the invention the corresponding partition coefficients are determined using the commercially available logP-calculation software of the company ACD (ACD Inc., 133 Richmond St. W., Suite 605, Toronto, ON, Canada M5H 2L3 z.B. in Perspectives in Drug Discovery and Design, 19: 99-116, 2000), which is based on the well characterized logP-contributions of single atoms, structural fragments and intramolecular interactions between fragments.

Alternatively, an experimental determination is possible using a water/n-octanol mixture at 25° C. (water: 50 ml, n-octanol: 50 ml, substances to be determined H—$R^{11}$ and H—$R^{12}$: 1 ml).

In a particularly preferred embodiment the residues $R^1$ are selected from the group consisting of:

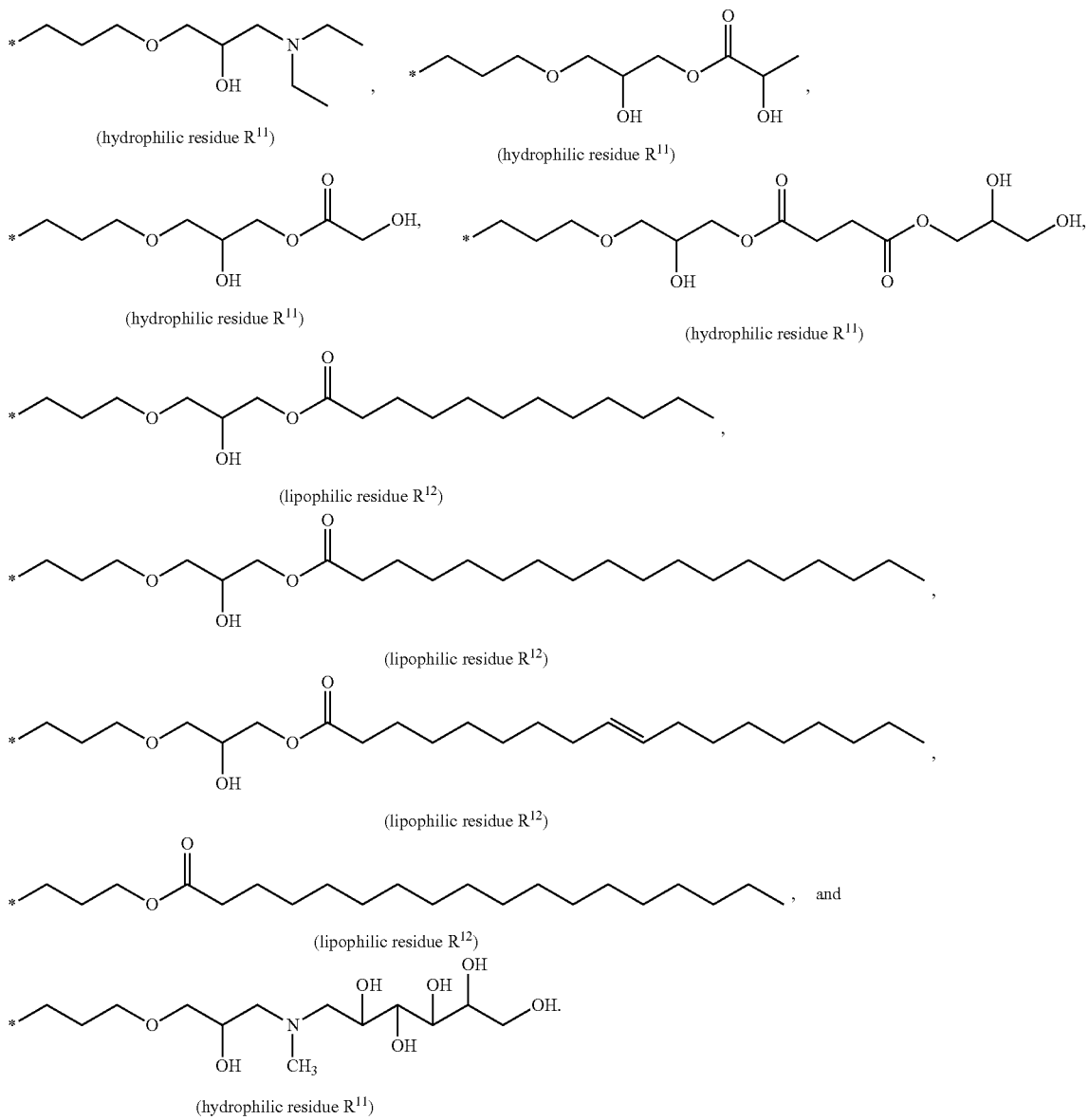

In a further preferred embodiment of the invention the radicals $R^1$ contain at least one ester moiety (—C(O)—O— or —O—C(O)—) and/or amino moiety (in particular —$NR^4R^5$, wherein $R^4$ and $R^5$ are each as defined above).

The polysiloxane compounds of the invention contain in a further preferred embodiment of the invention structural elements selected from the following formulae:

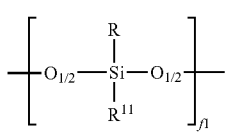

wherein R=$C_1$ to $C_{22}$ alkyl, fluoro $C_1$ to $C_{22}$ alkyl (which may include one or more fluorine atoms), $C_2$ to $C_{22}$ alkylene or aryl, preferably methyl, and $R^{11}$ is a hydrophilic residue as defined herein, and f1=0-300, preferably 0 to 200, more preferred 0 to 50, more preferred 0 to 30, even more preferred 0 to 10, specifically >0 to 1 (The indices as used herein represent average numbers determined by NMR-spectroscopy in particular).

$$\left[ -O_{1/2} - \underset{\underset{R^{12}}{|}}{\overset{\overset{R}{|}}{Si}} - O_{1/2} - \right]_{f2}$$

wherein R is as defined above, and $R^{12}$ is a lipophilic residue as defined herein, and f2=1-300, preferably 2 to 200, more preferred 2 to 50, most preferred 4 to 40,

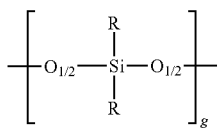

wherein the groups R can be identical or different, and are as defined above, and g=0-700, preferred 3 to 500, more preferred 5 to 200, more preferred 10 to 150,

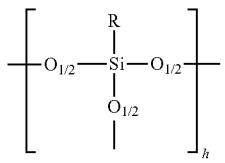

wherein R is as defined above, preferably methyl, and h=0-10, preferably 0,

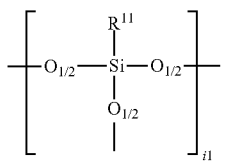

wherein $R^{11}$ is a hydrophilic residue as defined herein, and i1=0-5, preferably 0,

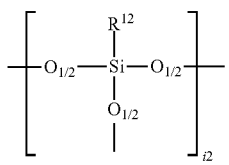

wherein $R^{12}$ is a lipophilic residue as defined herein, and i2=0-5, preferred 0,

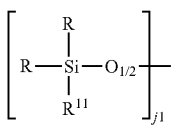

wherein R is as defined above, preferred methyl, and $R^{11}$ is hydrophilic residue as defined herein, and j1=0-15, preferably 0 to 2, more preferred 0,

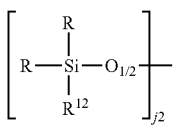

wherein R is as defined above, preferably methyl, and $R^{12}$ is a lipophilic residue as defined herein, and j2=0-15, preferred 0 to 2, more preferred 0,

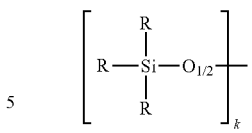

wherein R is as defined above, preferably methyl, and k=0-30, preferred 1 to 6, more preferred 2,

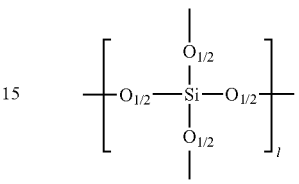

wherein l=0-10, preferred 0, f1+f2+g+h+i1+i2+j1+j2+k+l=12 to 1000, preferred 15 to 400, more preferred 20 to 200, more preferred 30 to 150.

Preferred organomodified silicones (d) to be used in accordance with the present invention are linear polydimethylsiloxanes with an average number of 50 to 200 siloxy units wherein part of the dimethylsiloxy units (preferably 10 to 30) is replaced by methyl($R^1$)siloxy units, wherein $R^1$ is preferably $R^{12}$ as defined herein. Preferably, the organomodified silicones (d) according to the invention represent linear trimethyl silyl terminated polysiloxane compounds.

The preferred molar ratio of the hydrophilic radicals $R^{11}$ and the lipophilic radicals $R^{12}$ in the organomodified silicones (d) according to the invention ranges from 5:1 to 1:200, more preferred from 2:1 to 1:150, more preferred from 1:1 to 1:120.

In another preferred embodiment of the invention the ratio between the hydrophilic radicals $R^{11}$ and the lipophilic radicals $R^{12}$ is 0. This means that in this case no hydrophilic radical $R^{11}$ is incorporated into the polysiloxane molecules.

The preferred molar ratio between the modified siloxy moieties containing $R^{11}$ and $R^{12}$ and the non modified siloxy moieties which contain exclusively R ranges from 5:1 to 1:20, preferred from 2:1 to 1:15, more preferred from 1:1 to 1:7.

In a further preferred embodiment of the organomodified silicones (d) used in accordance with the invention at least one, more than one or all of the following definitions are fulfilled:

R is selected from: $C_1$ to $C_{10}$-alkyl or $C_2$ to $C_{10}$ alkenyl, optionally substituted by 1 to 13 fluoro atoms, aryl, Z=divalent or trivalent straight chained, cyclic or branched, saturated or unsaturated $C_2$ to $C_{10}$ hydrocarbon radical, optionally containing one or more groups selected from —O—, and is substituted by one or more OH-Groups, or a bivalent or trivalent straight-chained, cyclic or branched, saturated or unsaturated $C_2$ to $C_{10}$-hydrocarbon residue, g=10 to 700, preferred 10 to 200, more preferred 10 to 150, more preferred 20 to 150, more preferred 30 to 150, more preferred 30 bis 100, f1=0 to 300, preferred 0 to 200, more preferred 0 to 50, more preferred 0 to 30, more preferred 0 to 10, specifically 0, f2=1 to 200, preferred 1 to 100, more preferred 1 to 50, more preferred 1 to 30, more preferred 3 to 30, more preferred 5 to 30, h=0 to 5 and preferred 0,
i1=0 to 5 and preferred 0,
i2=0 to 5 and preferred 0,
l=0 to 5 and preferred 0,
f1+f2+g+h+i1+i2+j1+j2+k+l =10 to 500, preferred 10 to 200, more preferred 10 to 150, more preferred 20 to 150, more preferred 30 to 150, more preferred 30 to 100, wherein for f1+i1+j1>0.

In a further preferred embodiment of the organomodified silicones (d) used according to the invention at least one, more than one or all of the following definitions are fulfilled:

Z=divalent or trivalent straight chained, cyclic or branched, saturated or unsaturated $C_2$ to $C_6$ hydrocarbon radical, optionally containing one or more groups selected from —O—, and substituted by one or more OH-Groups, or a bivalent or trivalent straight-chained, cyclic or branched, saturated or unsaturated $C_2$ to $C_6$-hydrocarbon residue, y=1, f1=0 to 300, preferred 0 to 200, more preferred 0 to 50, more preferred 0 to 30, more preferred 0 to 10, specifically 0, $R^2$=straight chained, cyclic or branched, saturated or unsaturated hydrocarbon radical with up to 30 carbon atoms, optionally containing one or more groups selected from —O—, —NH—, —$NR^3$—, —C(O)—, and optionally substituted by one or more OH-Groups, with $R^3$ as defined above.

In a further preferred embodiment of the organomodified silicones (d) used according to the invention they are characterized by:

R being replaced by at least one, preferably more than one groups $R^{11}$ and/or $R^{12}$, wherein $R^{11}$ is selected from a group consisting of:
$R^{11}$=—Z-(E)$_y$, wherein
E is selected from a group consisting of:
$E^{11}$=—O—C(O)—$R^{21}$, wherein $R^{21}$=straight chained, cyclic or branched, saturated or unsaturated C1 to C6 hydrocarbon radical, preferred C1 to C5 hydrocarbon radical, more preferred C1 to C4 hydrocarbon radical, even more preferred C1 to C3 hydrocarbon radical, specifically C1 and C2 hydrocarbon radical, optionally containing one or more groups selected from —O—, —NH—, —$NR^3$—, —C(O)—, and optionally substituted by one or more OH-Groups, wherein $R^3$=straight chained, cyclic or branched, saturated or unsaturated hydrocarbon radical with up to 6 carbon atoms, and $E^{21}$=—$NR^4R^5$, wherein $R^4$ and $R^5$ identical or different, selected from the group consisting of: hydrogen and straight chained, cyclic or branched, saturated or unsaturated C1 to C9 hydrocarbon radical, preferred C1 to C8 hydrocarbon radical, more preferred C1 to C6 hydrocarbon radical, even more preferred C1 to C4 hydrocarbon radical, specifically C1 to C2 hydrocarbon radical, optionally containing one or more groups selected from —O—, —NH—, —$NR^3$—, with $R^3$ as defined above, —C(O)—, and optionally substituted by one or more OH— and/or $NH_2$ groups, and $R^{12}$ selected from the group consisting of:
$R^{12}$=—Z-(E)$_y$, wherein
E=$E^{12}$=—O—C(O)—$R^{22}$, with
$R^{22}$=straight chained, cyclic or branched, saturated or unsaturated C7 to C22 hydrocarbon radical, preferred C10 to C22 hydrocarbon radical, more preferred C12 to C22 hydrocarbon radical, even more preferred C14 to C22 hydrocarbon radical, specifically C16 to C18 hydrocarbon radical, optionally containing one or more groups selected from —O—, —NH—, —$NR^3$—, —C(O)—, and optionally substituted by one or more OH-Groups, with $R^3$=straight chained, cyclic or branched, saturated or unsaturated hydrocarbon radical with up to 6 carbon atoms, and f1+f2+g+h+i1+i2+j1+j2+k+l=12 to 1000, preferred 15 to 400, more preferred 20 to 200, even more preferred 30 to 150, with f1=0-300, preferred 0-200, more preferred 0-50, even more preferred 0-30, specifically 0-10, more specifically 0, f2=1-300, preferred 2-200, more preferred 2-50, even more preferred 4-40, g=0-700, preferred 3-500, more preferred 5-200, even more preferred 10-100, j1=0-2, preferred 0 or 2,
j2=0-2, preferred 0 or 2,
k=0-2, preferred 0 or 2,
with j1+j2+k=2.

In a further embodiment part of the radical R are $R_L$, with $R_L$=C8 to C22, preferred C10 to C22, more preferred C14 to C22 alkyl, alkenyl, or fluoro alkyl (the number of carbon atoms refers to each of the residues alkyl, alkenyl or fluoro alkyl) or aryl, Preferably the number of the radicals $R_L \leq 5*(f1+f2+j1+j2)$, preferred $\leq 2*(f1+f2+j1+j2)$, more preferred $\leq 1*(f1+f2+j1+j2)$, even more preferred $\leq 0.5*(f1+f2+j1+j2)$, specifically $\leq 0.2*(f1+f2+j1+j2)$, and for f1+j1>0 f2 and j2 can be 0, $R_L$ preferably appears in the structures $$\left[ O_{1/2} - \underset{\underset{R_L}{|}}{\overset{\overset{R}{|}}{Si}} - O_{1/2} \right]_g$$

wherein in this case R is C1-C7 alkyl, alkenyl, or fluoro alkyl (the number of carbon atoms refers to each of the residues alkyl, alkenyl or fluoro alkyl), preferably methyl, and $$\left[ R - \underset{\underset{R_L}{|}}{\overset{\overset{R}{|}}{Si}} - O_{1/2} \right]_k .$$

In a further preferred embodiment the residue Z is selected from divalent or trivalent straight chained, cyclic or branched, saturated or unsaturated C2 to C10 hydrocarbon radical, preferred C3 to C6 hydrocarbon radical, more preferred C3 to C4 hydrocarbon radical, optionally containing one or more —O— groups and optionally substituted by one or more OH-groups, for example derived from propynyl, 1-butynyl and 2-butynediyl after hydrosilylation and having the structures Si∿CH=CH—$CH_2$—    $CH_2$=C(Si)—$CH_2$—

Si∿CH=CH—$CH_2$—$CH_2$—    $CH_2$=C(Si)—$CH_2$—$CH_2$—

—$CH_2$—C(Si)=CH—$CH_2$—.

In a further preferred embodiment of the invention one, more than one or all of the following definitions are fulfilled.

R, other than $R_L$, is selected from methyl, $R^{11}$ und $R^{12}$ are as defined above, Z=—CH$_2$CH$_2$CH$_2$—O—CH$_2$—, —CH$_2$CH$_2$CH$_2$—, and Z may be selected from cyclic structures, which are derived from cyclic epoxides,

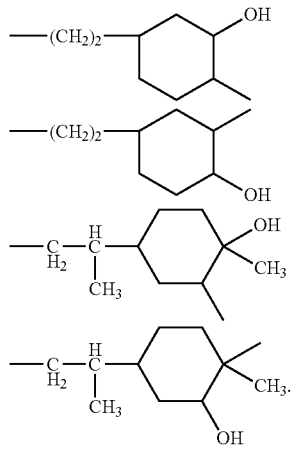

The organomodified silicones (d) of the invention may be synthesized according to the following procedures:
- (a) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines,
- (b) a saturated or unsaturated epoxy functional polysiloxane is reacted with a mixture, containing short chained, preferably hydroxy functionalized, carboxylic acids and long chained, preferably hydroxy free, carboxylic acids, and optionally afterwards with primary or secondary amines, wherein the carboxylic acids are obtained by partial esterification or amidation of carboxylic acid anhydrides with corresponding alcohols or amines,
- (c) a saturated or unsaturated epoxy functional polysiloxane is reacted with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
- (d) a SiH functionalized polysiloxane is reacted with one or more than one monofunctional acetylenically unsaturated ether of glycerol or glycerol oligomers, optionally having silylated, acetylated, ketalized or esterified OH groups, and one or more than one ester of fatty acids with olefinically or acetylenically unsaturated alcohols
- (e) a SiH functionalized polysiloxane is reacted with one or more than one monofunctional olefinically unsaturated ether of glycerol or glycerol oligomers, optionally having silylated, acetylated, ketalized or esterified OH groups, and one or more than one ester of fatty acids with acetylenically unsaturated alcohols
- (f) a SiH functionalized polysiloxane is reacted with one or more than one monofunctionally unsaturated alkyne or alkene and one or more than one monofunctional olefinically or acetylenically unsaturated epoxide and subsequently with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
- (g) a SiH functionalized polysiloxane is reacted with one or more than one monofunctionally unsaturated alkyne and one or more than one monofunctional olefinically or acetylenically unsaturated epoxide and subsequently with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
- (h) a SiH functionalized polysiloxane is reacted with one or more than one monofunctionally unsaturated alkyne or alkene and one or more than one monofunctional olefinically or acetylenically unsaturated epoxide and one or more than one olefinically or acetylenically unsaturated fatty acid ester and subsequently with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
- (i) a SiH functionalized polysiloxane is reacted with one or more than one monofunctional olefinically or acetylenically unsaturated epoxide and one or more than one olefinically or acetylenically unsaturated fatty acid ester and subsequently with a mixture, containing short chained, preferably hydroxy functionalized, carboxylic acids and long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines,
- (j) a SiH functionalized polysiloxane is reacted with one or more than one monofunctionally unsaturated alkyne or alkene and one or more than one monofunctional olefinically or acetylenically unsaturated epoxide and one or more than one olefinically or acetylenically unsaturated fatty acid ester and subsequently with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines,
- (k) a SiH functionalized polysiloxane is reacted with one or more than one monofunctional olefinically or acetylenically unsaturated epoxide and one or more than one olefinically or acetylenically unsaturated fatty acid ester and subsequently with short chained, preferably hydroxy functionalized, carboxylic acids, and optionally afterwards with primary or secondary amines, wherein optionally the carboxylic acids can be obtained by partial esterification or amidation of carboxylic acid anhydrides with corresponding alcohols or amines, (l) a SiH functionalized polysiloxane is reacted with one or more than one monofunctionally unsaturated alkyne or alkene and one or more than one monofunctional olefinically or acetylenically unsaturated epoxide and one or more than one olefinically or acetylenically unsaturated fatty acid ester and subsequently with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (m) a SiH functionalized polysiloxane is reacted with one or more than one monofunctionally unsaturated alkyne or alkene and one or more than one monofunctional olefinically unsaturated epoxide and one or more than one acetylenically unsaturated fatty acid ester and subsequently with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (n) a SiH functionalized polysiloxane is reacted with one or more than one monofunctional acetylenically unsaturated epoxide and one or more than one acetylenically or olefinically unsaturated fatty acid ester and subsequently with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (o) a SiH functionalized polysiloxane is reacted with one or more than one monofunctional olefinically unsaturated epoxide and one or more than one acetylenically unsaturated fatty acid ester and subsequently with long chained, preferably hydroxy free, carboxylic acids, and optionally afterwards with primary or secondary amines, wherein optionally the carboxylic acids can be obtained by partial esterification or amidation of carboxylic acid anhydrides with corresponding alcohols or amines, (p) an aminofunctional polysiloxane is reacted with short chained and/or long chained carboxylic acid esters, lactones, carboxylic acid halides or carboxylic acid silyl esters, and (q) an aminofunctional polysiloxane is reacted with short chained and/or long chained alkyl or aryl substituted carbonates an aminofunctional polysiloxane is reacted with short chained and/or long chained alkyl substituted epoxides.

In order to incorporate the hydrophilic radial $R^{11}$ the above described reactive intermediates, especially epoxy and amino functionalized intermediates, can be reacted with i.e.

hydroxy functionalized short chained carboxylic acids,
hydroxy functions containing partial esters or amides of dicarboxylic acides, like succinic acid or it's anhydride,
primary or secondary amines, preferably hydroxyl groups containing primary and secondary amines or
at least one primary or secondary amino group and at least one hydroxyl group containing aminoamides,
short chained epoxides and cyclocarbonates.

Examples for hydroxyl groups containing carboxylic acids are monohydroxy as well as polyhydroxy carboxylic acids, like glycolic acid, lactic acid, gamma-hydroxy butyric acid, 2,3-dihydroxy propionic acid, alpha,beta-dihydroxy butyric acid, alpha,gamma-dihydroxy butyric acid, gluconic acid, glucopyranosyl arabinonic acid. It is within the scope of the invention to use the acids in form of their esters, specifically methyl esters, lactones, i.e. gamma-butyro lactone, gluconic acid lactone and glucopyranosyl arabinonic acid lactone.

The usage of carboxylic acids bearing more than one carboxylic acid function like mucic acid and glucaric acid is possible but less preferred.

Alternatively, esters or amides containing at lest one hydroxyl group and one carboxylic acid group can be used to incorporate the hydrophilic radical $R^{11}$.

In a preferred embodiment of the invention monoesters of dicarboxylic acids are used. Examples for dicarboxylic acids are oxalic acid, succinic acid, maleic acid, fumaric acid, phthalic acid, terephthalic acid. It is within the scope of the invention to esterify or amidate the acids in form of their anhydrides. The alcohols used are at least difunctional ones having a chain length of C2. Examples are 1,2-propane diol, 1,3-propane diol, glycerol, pentaerythrol and sorbitol. It is within the scope of the invention to esterify the alcohols in form of their epoxides with the acids. An example is glycidol.

The aminoalcohols used are at least difunctional ones having a chain length of ≥C2. Examples are ethanolamine, diethanolamine, 1-amino-(2-hydroxy)-propane, 1-amino-(3-hydroxy)-propane, 1-amino-2,3-dihydroxypropane, glucamine, N-methyl-glucamine.

The usage of tri- and higher valent carboxylic acids is possible but less preferred. An example is trimellitic acid, which can be used as mono carboxylic acid diester structure starting from trimellitic acid anhydride mono acid chloride. Another example is pyromellitic acid dianhydride, yielding preferably dicarboxylic acid diester structures.

An example for a secondary amines is diethylamine. Examples for hydroxyl groups containing primary and secondary amines are ethanolamine, diethanolamine, 1-amino-(2-hydroxy)-propane, 1-amino-(3-hydroxy)-propane, 1-amino-2,3-dihydroxy-propane, glucamine, N-methylglucamine.

The aminoamides can be preferably synthesized from primary-secondary amines with lactones, specifically hydroxy functionalized lactones. Examples for primary-secondary amines are $H_2NCH_2CH_2NHCH_2CH_2NH_2$ and $H_2NCH_2CH_2CH_2NHCH_2CH_2CH_2NH_2$. Examples for preferred lactones are gamma-butyric acid lactone, gluconic acid lactone, glucopyranosyl arabinonic acid lactone. Examples for short chained epoxides and cyclocarbonates are glycidol and glycidol carbonate.

In order to incorporate the lipophilic radical $R^{12}$ the above mentioned reactive intermediates, especially epoxy and amino functionalized intermediates, preferably react with carboxylic acids;
at least one carboxylic acid group containing esters or amide,
long chained primary or secondary amines;
at least one primary or secondary amino group and at least one long chained alkyl group containing aminoamides; or
long chained epoxides and cyclocarbonates.

In the context of the invention these carboxylic (fatty) acids are preferably monofunctional carboxylic acids. Examples are acetic acid, butyric acid, hexanoic acid, 2-ethyl hexanoic acid, dodecanoic acid, tetradecanoic acid, hexadecanoic acid, octadecanoic acid, undecenic acid, oleic acid, linolic acid, linolenic acid. The usage of long chained hydroxy carboxylic acids like ricinolic acid is possible but less preferred.

In a preferred embodiment monofunctional carboxylic acids≥C10 are used to incorporate the lipophilic radical $R^{12}$.

The usage of long chained lactones like 5-dodecanolide is possible.

Alternatively, at least one carboxylic acid group containing esters or amides can be used to incorporate the radicals $R^{12}$.

In a preferred embodiment of the invention monoesters of dicarboxylic acids are used. Examples for dicarboxylic acids are oxalic acid, succinic acid, maleic acid, fumaric acid, phthalic acid, terephthalic acid. It is within the scope of the invention to esterify the acids in form of their anhydrides. Preferred examples for the alcohols are monohydroxy alcohols like 2-ethylhexanol, dodecanol, undecenol, tridecanol, hexadecanol, oleyl alcohol, octadecanol, ethanol, 2-propanol, 2-ethylhexanol, dodecanol, undecenol, isotridecanol, hexadecanol, oleylalkohol, octadecanol, $HOCH_2CH_2(CF_2)_5CF_3$ and $HO(CH_2)_6Si(CH_3)_3$. It is within the scope of the invention to esterify alcohols in form of their epoxides, i.e. dodecene oxide and alkyl (C12-C14) glycidyl ether, with diacids. Preferred examples for the amines are 2-ethylhexylamine, dodecylamine, undecenylamine, hexadecenylamine, oleylamine, and stearylamine.

The usage of tri- and higher valent carboxylic acids is possible but less preferred. An example is trimellitic acid, which can be used as mono carboxylic acid diester structure starting from trimellitic acid anhydride mono acid chloride. Another example is pyromellitic acid dianhydride, yielding preferably dicarboxylic acid diester structures.

An example for a secondary amines is bis-ethylhexylamine.

The aminoamides can be preferably synthesized from primary-secondary amines with long chained lactones, specifically hydroxy functionalized lactones. Examples for primary-secondary amines are $H_2NCH_2CH_2NHCH_2CH_2NH_2$ and $H_2NCH_2CH_2CH_2NHCH_2CH_2CH_2NH_2$. An example for a preferred long chained lactone is 5-dodecanolide.

Examples for long chained epoxides and cyclocarbonates are alkyl (C12-C14) glycidyl ethers and the long chained fatty acid esters and fatty alcohol ethers of glycerol carbonate.

It is within the scope of the invention to react the epoxy or amino functionalized intermediates with one or more than one hydrophilic components and/or one or more than one lipophilic components in order to incorporate the radical $R^{11}$ and/or the radical $R^{12}$.

In a preferred embodiment of the invention the epoxy or amino functionalized intermediates react with a mixture of hydrophilic and lipophilic carboxylic acid compounds.

In a preferred embodiment of the invention the epoxy or amino functionalized intermediates react with a mixture of hydrophilic amino compound and a lipophilic carboxylic acid compound.

In another preferred embodiment of the invention the epoxy or amino functionalized intermediates react with the hydrophilic carboxylic acid or amino compound first and afterwards with the lipophilic carboxylic acid compound. The opposite order of addition is also possible.

The usage of the above described concepts on
one or more than one hydrophilic/lipophilic acid
different addition strategies
yields products containing different polymer compositions.

The molar ratio Σ (epoxide (or amine)) on silicone: Σ (carboxylic acid and amino components) ranges from 1:1 to 1:2, preferred 1:1 to 1:1.5, more preferred 1:1 to 1:1.1.

The molar ratio of the structural elements is important to adjust the properties of the polysiloxane copolymer as W/O emulsifier, i.e. with respect to the chemical structure of the oil to be emulsified and the target ratio water phase:oil phase.

In general, an increase in conventional, non-modified siloxy units yields a better compatibility with siloxane based oil phases.

Further, in general, an increase in the number of hydrophilic moieties yields a better compatibility with the water phase.

Still further, in general, an increase in the number of lipophilic moieties yields a better compatibility with hydrocarbon based oil phases.

The organomodified silicones (d) free of poly(oxyalkylated) moieties according to the present invention are preferably formulated in concentrations ranging from 0.1% to 20% by weight relative to the total weight of the composition, and more particularly in an amount ranging from 0.5% to 10%, more specifically 0.5% to 5%.

The organic UV-screening agents in accordance with this invention may be selected, in particular, from among the organic UV-screening agents of the oxanilide type, of the triazine type, of the triazole type, of the vinylamide type, of the cinnamide type, of the aminophenylbenzothiazole type, of the benzophenone type and of the merocyanine type.

Preferably these organic UV-screening agents are essentially insoluble in the UV-photo-protecting cosmetic composition, i.e. essentially insoluble in the aqueous phase as well as in the fatty phase. For example, the solubility in water is preferably less than 0.5% by weight more preferably less than 0.1% by weight at 25° C. The solubility in most of the organic solvents, including the fatty phase ingredients, such as paraffin oil, fatty alcohol benzoates and fatty acid triglycerides is less than 5% by weight, preferably less than 1% by weight at 25° C.

Exemplary UV-screening agents of the oxanilide type include those having the structural formula (1):

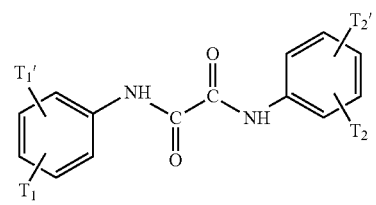

in which $T_1$, $T_{1'}$, $T_2$ and $T_{2'}$, which may be identical or different, are each a C1-C8-alkyl radical or a C1-C8-alkoxy radical. These compounds are described in WO95/22959.

Examples thereof are the commercial products TINUVIN 315 and TINUVIN 312 marketed by Ciba-Geigy and respectively having the structural formulae:

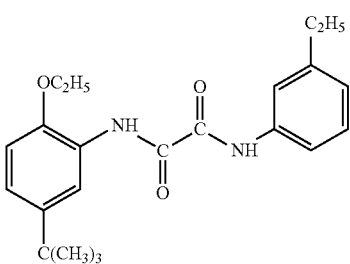

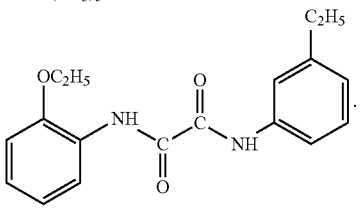

Triazine derivatives in accordance with the invention are 2,4,6-tris[p-(2'-ethylhexyl-1'-oxycarbonyl)panilino]-1,3,5-triazine in micronized form or the compound having the structural formula

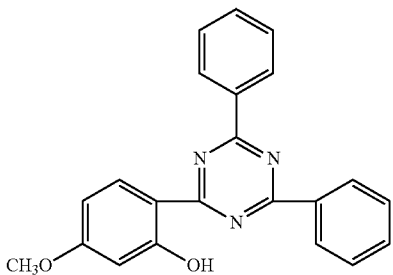

also in micronized form.

The preferred 1,3,5-triazine derivatives in accordance with the invention have the following structural formula (2)

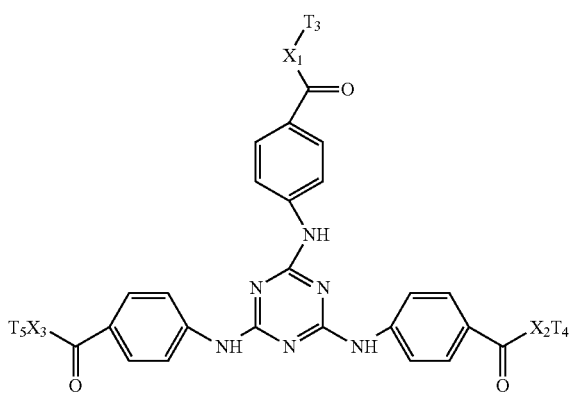

in which $X_1$, $X_2$ and $X_3$, which may be identical or different, are each an oxygen atom or a radical —N—Y—; the radicals Y, which may be identical or different, are each hydrogen or a linear or branched C1-C18 alkyl radical, a C5-C12 cycloalkyl radical optionally substituted with one or more C1-C4 alkyl radicals; T3, T4 and T5, which may be identical or different, are each hydrogen, an alkali metal, an ammonium radical which is optionally substituted with one or more alkyl or hydroxyalkyl radicals, a linear or branched C1-C18 alkyl radical, a C5-C12 cycloalkyl radical which is optionally substituted with one or more C1-C4 alkyl radicals, a polyoxyethylenated radical having from 1 to 6 ethylene oxide units and whose terminal OH group is methylated or a radical of the following formulae (3), (4) or (5):

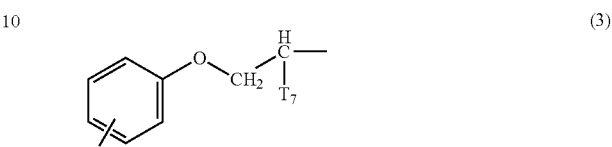

in which T6 is hydrogen or a methyl radical; T7 is a C1-C9-alkyl radical; p is an integer ranging from 0 to 3; q is an integer ranging from 1 to 10; A is a C4-C8-alkyl radical or a C5-C8-cycloalkyl radical; B is a linear or branched C1-C8-alkyl radical, a C5-C8-cycloalkyl radical, an aryl radical which is optionally substituted with one or more C1-C4-alkyl radicals; and T8 is hydrogen or a methyl radical.

A first preferred family of 1,3,5-triazine derivatives is that which is, in particular, described in EP-A-0,517,104 (expressly incorporated by reference herein), and the 1,3,5-triazines having the above formula (2) while satisfying all of the following characteristics:

(i) X1, X2 and X3 are identical and are each an oxygen atom;

(ii) T3 is a C5-C12-cycloalkyl radical which is optionally substituted with one or more C1-C4-alkyl radicals, a radical of formula (3), (4) or (5) above in which B is a C1-C4-alkyl radical, and T8 is the methyl radical;

(iii) T4 and T5, which may be identical or different, are each hydrogen, an alkali metal, an ammonium radical which is optionally substituted with one or more alkyl or hydroxyalkyl radicals, a linear or branched C1-C18-alkyl radical, a C5-C12-cycloalkyl radical which is optionally substituted with one or more C1-C4-alkyl radicals, or a radical of formula (3), (4) or (5) above in which B is a C1-C4-alkyl radical and T8 is a methyl radical.

A second preferred family of 1,3,5-triazine derivatives according to the invention is that, in particular, described in EP-A-0,570,838 (also hereby expressly incorporated by reference), and the 1,3,5-triazines having the formula (2) and satisfying all of the following characteristics:

(i) X1 is an oxygen atom, X2 is the —NH— radical or an oxygen atom, and X3 is the —NH— radical;

(ii) T5 is a linear or branched C1-C18-alkyl radical, or a C5-C12-cycloalkyl radical which is optionally substituted with one or more C1-C4-alkyl radicals;

(iii) T3 is hydrogen, an alkali metal, an ammonium radical, a radical of formula (5), a linear or branched C1-C18-alkyl radical, a C5-C12-cycloalkyl radical which is optionally substituted with one or more C1-C4-alkyl radicals, with the proviso that if X2 is the —NH— radical, then T4 is a linear or branched C1-C18-alkyl radical, or a C5-C12-cycloalkyl radical which is optionally substituted with one or more C1-C4 alkyl radicals; and with the further proviso that if X2 is an oxygen atom, then T4 is hydrogen, an alkali metal, an ammonium radical, a radical of formula (5), a linear or branched C1-C18 alkyl radical, or a C5-C12 cycloalkyl radical which is optionally substituted with one or more C1-C4 alkyl radicals.

A third preferred family of 1,3,5-triazine derivatives according to the invention is that, in particular, described in EP-A-0,796,851 (also expressly incorporated by reference), and the 1,3,5-triazines having the formula (2) and satisfying all of the following characteristics:

(i) X1, X2 and X3 are each —NY—;

(ii) the radicals Y, which may be identical or different, are each hydrogen or a linear or branched C1-C18-alkyl radical, or a C5-C12-cycloalkyl radical which may be substituted with one or more C1-C4-alkyl radicals;

(iii) T3, T4 and T5, which may be identical or different, are each hydrogen or a radical Y.

These organic UV-screening agents of the triazine type are described in U.S. Pat. No. 4,617,390 and in EP-0,517,104, EP-0,570,838 and EP-0,796,851 (expressly incorporated by reference).

Exemplary UV-screening agents of the triazine type of formula (2) are, more particularly:

2,4,6-tris[p-(2'-ethylhexyl-1'-oxycarbonyl)anilino]-1,3,5-triazine which is a screening agent known per se, active in the UV-B range, existing in solid form, and which is marketed, in particular, under the trademark "UVINUL T150" by BASF this product has the following structural formula:

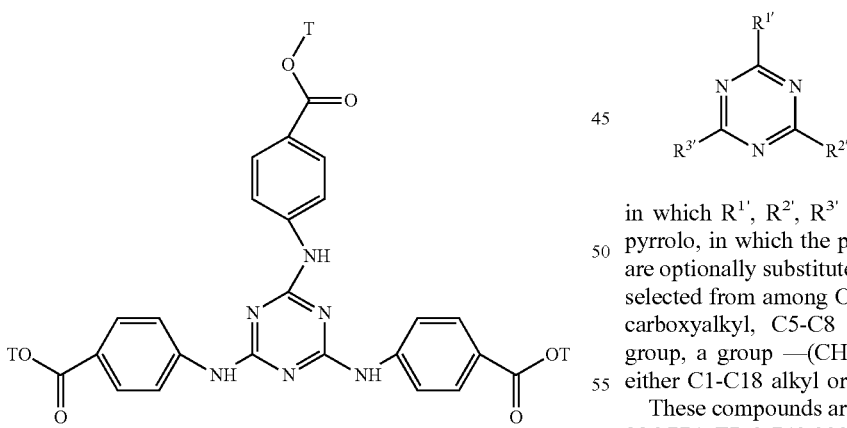

in which T is a 2-ethylhexyl radical; and

2-[(p-(tert-butylamido)anilino]-4,6-bis[(p-(2'-ethylhexyl-1'-oxycarbonyl)panilino]-1,3,5-triazine, having the following structural formula:

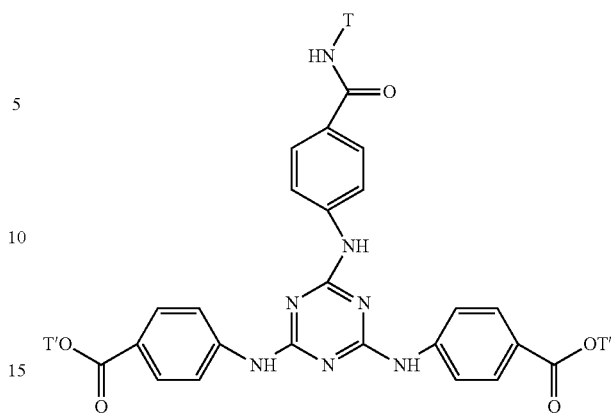

in which T' is a 2-ethylhexyl radical and T is a tert-butyl radical.

Also exemplary insoluble UV-screening agents of the triazine type in accordance with the invention are the insoluble derivatives of s-triazine substituted by benzalmalonate and/or phenylcyanoacrylate groups, such as those described in EP-A-0,790,243 (also expressly incorporated by reference).

Among these UV-screening agents of the triazine type, the following compounds are more particularly exemplary:

2,4,6-tris(diethyl 4'-aminobenzalmalonate)-s-triazine, 2,4,6-tris(diisopropyl 4'-aminobenzalmalonate)-s-triazine;

2,4,6-tris(dimethyl 4'-aminobenzalmalonate)-s-triazine;

2,4,6-tris(ethyl [alpha]-cyano-4-aminocinnamate)-s-triazine.

Among the insoluble UV-screening agents of the triazine type in accordance with the invention are those having the following structural formula (6):

$$\text{(6)}$$

$$\underset{R^{3'}}{\overset{R^{1'}}{\underset{N}{\overset{N}{\bigtriangleup}}}}\phantom{xx}R^{2'}$$

in which $R^{1'}$, $R^{2'}$, $R^{3'}$ are independently phenyl, phenoxy, pyrrolo, in which the phenyl, phenoxy and pyrrolo radicals are optionally substituted with one, two or three substituents selected from among OH, C1-C18 alkyl or alkoxy, C1-C18 carboxyalkyl, C5-C8 cycloalkyl, a methylidenecamphor group, a group —(CH=CH)$_n$(CO)—OR$^{4'}$, wherein R$^{4'}$ is either C1-C18 alkyl or cinnamyl, and n is equal to 0 or 1.

These compounds are described in WO-97/03,642, GB-2,286,774, EP-0-743,309, WO-98/22,447, GB-2,319,523 (expressly incorporated by reference).

Among the insoluble UV-screening agents of the triazine type in accordance with the invention, exemplary are the insoluble derivatives of s-triazine substituted by benzotriazole and/or benzothiazole groups, such as those described in WO-98/25,922 (also expressly incorporated by reference).

More particularly exemplary are:

2,4,6-tris[(3'-benzotriazol-2-yl-2'-hydroxy-5'-methyl) phenylamino]-s-triazine; and 2,4,6-tris[(3'-benzotriazol-2-yl-2'-hydroxy-5'-ter-octyl)phenylamino]-s-triazine.

Exemplary organic UV-screening agents of the triazole type in accordance with the invention are those of the following structural formula (7) as described in WO-95/22,959 (also expressly incorporated by reference):

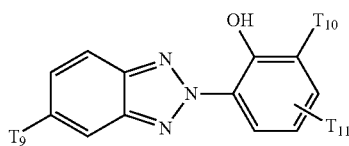

(7)

in which T9 is a hydrogen atom or a C1-C18 alkyl radical; and T10 and T11, which may be identical or different, are each a C1-C18 alkyl radical which is optionally substituted with a phenyl radical.

Exemplary compounds of formula (7) are the commercial products TINUVIN 328, 320, 234 and 350 marketed by Ciba-Geigy having the following structural formulae:

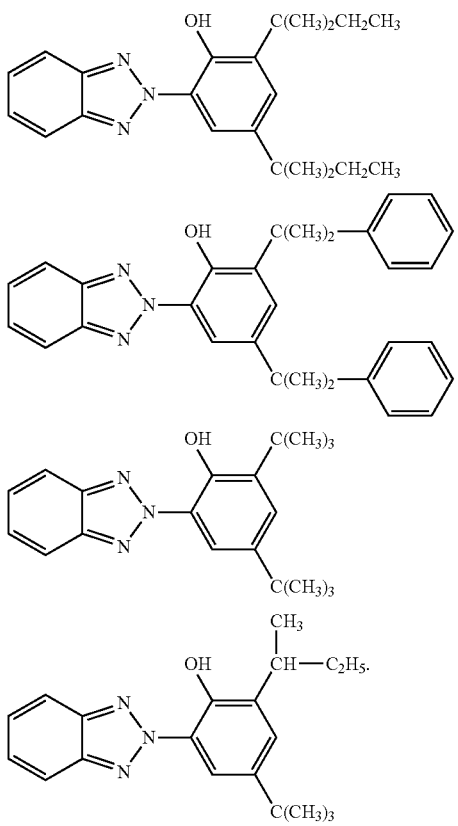

Exemplary organic UV-screening agents of the triazole type in accordance with the invention are the compounds described in U.S. Pat. Nos. 5,687,521, 5,687,521, 5,373,037, 5,362,881 and, in particular, [2,4'-dihydroxy-3-(2H-benzotriazol-2-yl)-5-(1,1,3,3-tetramethylbutyl)-2'-n-octoxy-5'-3-(2H-benzotriazol-2-yl)-5-(1,1,3,3-tetramethylbutyl)-2'-n-octoxy-5'-benzoyl]diphenylmethane marketed under the trademark MIXXIM PB30 by Fairmount Chemical and having the structural formula:

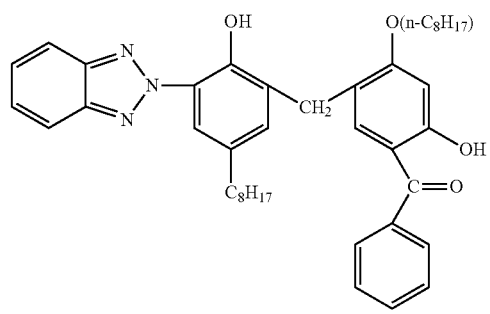

and exemplary organic UV-screening agents of the benzotriazole type in accordance with the invention are the methylenebis(hydroxyphenyl-benzotriazole) compounds having the following structural formula:

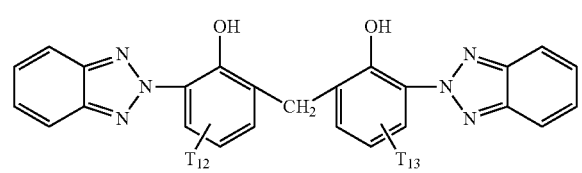

in which the radicals T12 and T13, which may be identical or different, are each a C1-C18 alkyl radical which may be substituted with one or more radicals selected from among a C1-C4 alkyl, a C5-C12 cycloalkyl, or an aryl radical. These compounds are per se known and are described in U.S. Pat. Nos. 5,237,071 and 5,166,355, GB-A-2,303,549, DE-197,26,184 and EP-A-893,119 (also expressly incorporated by reference).

In formula (8) above, the C1-C18 alkyl radicals may be linear or branched and include, for example, methyl, ethyl, n-propyl, isopropyl, n-butyl, isobutyl, tert-butyl, tert-octyl, n-amyl, n-hexyl, n-heptyl, n-octyl, iso-octyl, n-nonyl, n-decyl, n-undecyl, n-dodecyl, tetradecyl, hexyldecyl or octadecyl; the C5-C12 cycloalkyl radicals include, for example, cyclopentyl, cyclohexyl, cyclooctyl; and the aryl radicals include, for example, phenyl or benzyl.

Among the compounds of formula (8), those having the following structural formula are particularly preferred:

compound (a)

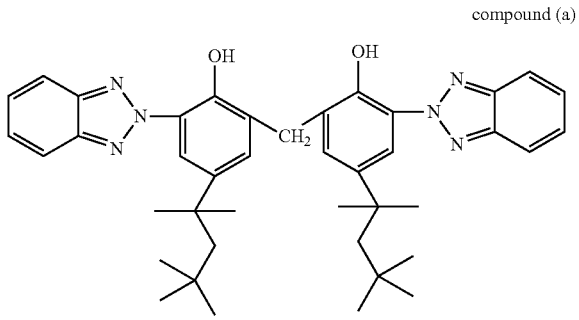

compound (b)

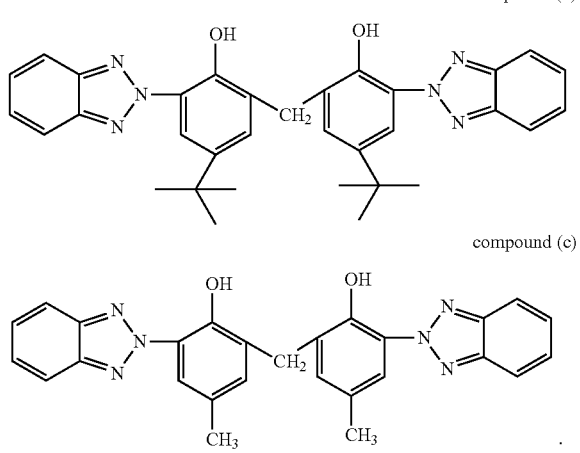

compound (c)

The compound (a) with the nomenclature 2,2'-methylenebis[6-(2H-benzotriazol-2-yl)-4-(1,1,3,3-tetramethylbutyl) phenol] is marketed under the trademark MIXXIM BB/100 by Fairmount Chemical. It is marketed in micronized form under the trademark TINOSORB M by Ciba-Geigy.

The compound (c) with the nomenclature 2,2'-methylenebis[6-(2H-benzotriazol-2-yl)-4-(methyl)phenol] is marketed under the trademark MIXXIM BB/200 by Fairmount Chemical.

Among the organic screening agents of the vinylamide type in accordance with the invention, exemplary are the compounds of the following formulae which are described in WO-95/22,959 (expressly incorporated by reference):

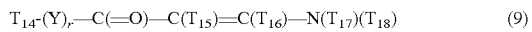

$T_{14}$-(Y)$_r$—C(=O)—C($T_{15}$)=C($T_{16}$)—N($T_{17}$)($T_{18}$)    (9)

in which T14 is a C1-C18, preferably C1-C5, alkyl radical or a phenyl group which is optionally substituted with one, two or three radicals selected from among OH, C1-C18 alkyl, C1-C8 alkoxy, or a radical —C(=O)—O$T_{19}$ wherein T19 is a C1-C18 alkyl radical; T15, T16, T17 and T18, which may be identical or different, are each a C1-C18, preferably C1-C5, alkyl radical or a hydrogen atom; Y is N or O and r is equal to 0 or 1.

Among these compounds, particularly representative are:
4-octylamino-3-penten-2-one;
ethyl 3-octylamino-2-butenoate;
3-octylamino-1-phenyl-2-buten-1-one;
3-dodecylamino-1-phenyl-2-buten-1-one.

Exemplary insoluble organic screening agents of the cinnamamide type are those compounds described in WO-95/22,959 (expressly incorporated by reference) and having the following structural formula:

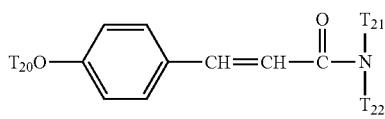

in which $T_{20}$ is a hydroxyl or C1-C4 alkoxy, preferably methoxy or ethoxy, radical; $T_{21}$ is hydrogen, C1-C4 alkyl, preferably methyl or ethyl; $T_{22}$ is a radical —(CONH)$_s$-phenyl wherein s is equal to 0 or 1 and the phenyl group may be substituted with one, two or three groups selected from among OH, C1-C18 alkyl, C1-C8 alkoxy, or a radical —C(=O)—O$T_{23}$ wherein $T_{23}$ is a C1-C18 alkyl and more preferably $T_{23}$ is a phenyl, 4-methoxyphenyl or phenylaminocarbonyl group.

Also exemplary are the cinnamamide dimers such as those described in U.S. Pat. No. 5,888,481, for example, the compound having the structural formula:

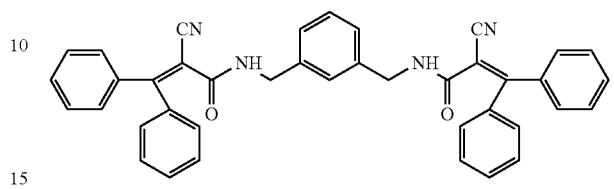

Another specific family of insoluble organic UV-screening agents in accordance with the invention are the polyvalent metal salts (for example $Ca^{2+}$, $Zn^{2+}$, $Mg^{2+}$, $Ba^{2+}$<, $Al^{3+}$ or $Zr^{4+}$) of sulfonic or carboxylic organic screening agents such as the polyvalent metal salts of sulfonated derivatives of benzylidenecamphor, for example those described in FR-A-2,639,347; the polyvalent metal salts of sulfonated derivatives of benzimidazole, for example those described in EP-A-893,119; and the polyvalent metal salts of cinnamic acid derivatives, for example those described in JP-87/166,517.

Also representative are the metal or ammonium or substituted ammonium complexes of organic UV-A and/or UV-B screening agents as described in WO-93/10,753, WO-93/11,095 and WO-95/05,150.

Exemplary UV-screening agents of the aminophenylbenzothiazole type include those having the structural formula (11):

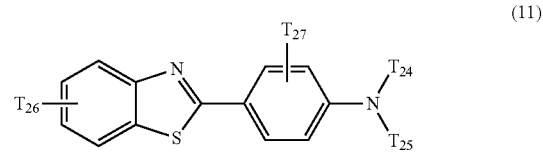

in which $T_{24}$ and $T_{25}$ are each independently of the other hydrogen; unsubstituted or halo-, amino-, mono- or di-C1-C5 alkylamino-, cyano- or C1-C5 alkoxy-substituted C1-C22 alkyl, C5-C10 cycloalkyl, carboxy-C1-C22 alkyl, carboxy-C6-C10 aryl, C8-C10 aryl or C6-C10 aryl-C1-C5 alkyl; carbamoyl; or sulfamoyl; or T24 and T25, together with the nitrogen atom linking them, form a 5- to 7-membered heterocyclic radical; and $T_{26}$ is hydrogen; or C1-C22 alkyl; and $T_{27}$ is hydrogen; hydroxy; C1-C22 alkyl; or C1-C22 alkoxy.

These compounds are described in US 2005/0175554 (expressly incorporated by reference).

Among the compounds of formula (11), those having the following structural formula are particularly preferred:

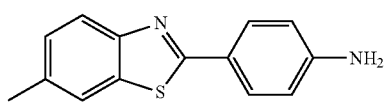

-continued

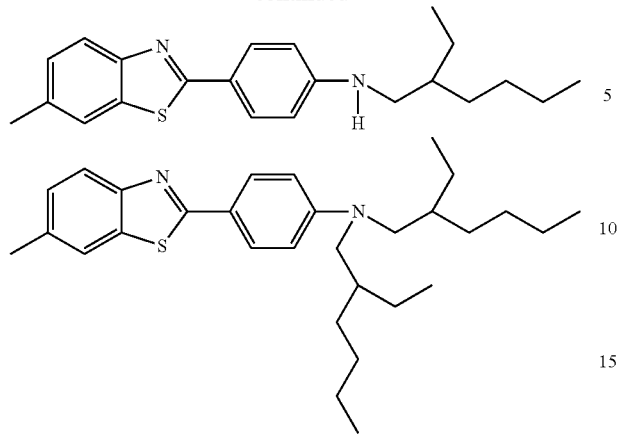

Exemplary UV-screening agents of the benzophenone type include those having the structural formula (12):

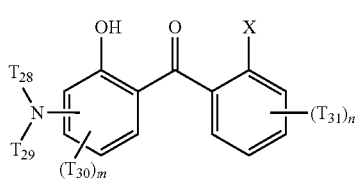

(12)

in which $T_{28}$ and $T_{29}$, independently from each other are hydrogen; C1-C20 alkyl; C2-C10 alkenyl; C3-C10 cycloalkyl; C3-C10 cycloalkenyl; or T28 and T29 together with the nitrogen atom to which they are bonded can form a 5- or 6-membered ring; $T_{30}$ and $T_{31}$, independently from each other are C1-C20 alkyl; C2-C10 alkenyl; C3-C10-cycloalkyl; C3-C10 cycloalkenyl; C1-C12 alkoxy; C1-C20 alkoxycarbonyl; C1-C12 alkylamino; C1-C12 dialkylamino; C6-C10 aryl; C6-C10 heteroaryl, optionally substituted, substituents which confer solubility in water, chosen from the group consisting of a nitrile group, carboxylate, sulfonate or ammonium radicals;

X is hydrogen; —$COOT_{32}$; —$CONT_{33}T_{34}$; wherein $T_{32}, T_{33}$ and $T_{34}$, independently from each other are hydrogen; C1-C20 alkyl; C2-C10 alkenyl; C3-C10 cycloalkyl; C3-C10 cycloalkenyl; or $(Q^1\text{-}O)_o\text{-}Q^2$-aryl;

$Q^1$ is —(CH2)2-; —(CH2)3; —(CH2)4-; —CH(CH3)—CH2-;

$Q^2$ is —CH2—CH3; —CH2—CH2—CH3; —CH2—CH2—CH2—CH3; —CH(CH3)—CH3;

m is a number from 0 to 3;

n is a number from 0 to 4; and o is a number from 1 to 20.

Among the compounds of formula (12), the one having the following structural formula is particularly preferred:

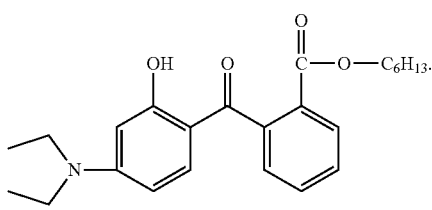

These compounds are described in US 2007/0219275 (expressly incorporated by reference).

Exemplary UV-screening agents of the merocyanine type include those having the structural formula (13):

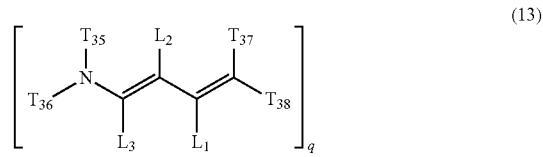

(13)

in which $T_{35}$ and $T_{36}$ independently of each other are hydrogen; C1-C22 alkyl; C2-C22 alkenyl, C2-C22 alkinyl, C3-C12 cycloalkyl, C3-C12 cycloalkenyl, C7-C20 aralkyl, C1-C20 heteroalkyl, C3-C12 cycloheteroalkyl, C5-C11 heteroaralkyl, C6-C20 aryl, C4-C9 heteroaryl, —$COT_{44}$ or —$CONT_{44}T_{45}$; $T_{37}$ is CN; —$COOT_{39}$; —$CONHT_{39}$; —$COT_{39}$; —$SO_2T_{39}$; —$CONT_{39}T_{40}$, C6-C20 aryl; or C4-C9 heteroaryl; $T_{38}$ is CN; —$COOT_{41}$; —$CONHT_{41}$; —$COT_{41}$; —$SO_2T_{41}$; —$CONT_{41}T_{42}$; C1-C22 alkyl; C2-C22 alkenyl; C2-C22 alkinyl; C3-C12 cycloalkyl; C3-C12 cycloalkenyl; C7-C20 aralkyl; C1-C20 heteroalkyl; C3-C12 cycloheteroalkyl; C5-C11 heteroaralkyl; C6-C20 aryl; or C4-C9 heteroaryl;

$T_{39}$, $T_{40}$, $T_{41}$, $T_{42}$ independently of each other are hydrogen; C1-C22 alkyl; C2-C22 alkenyl; C2-C22 alkinyl; C3-C12 cycloalkyl; C3-C12cycloalkenyl; C7-C20 aralkyl; C1-C20 heteroalkyl, C3-C12 cycloheteroalkyl; C5-C11 heteroaralkyl; C6-C20 aryl; C4-C9 heteroaryl; $SiT_{46}T_{47}T_{48}$; $Si(OT_{46})(OT_{47})(OT_{48})$, $SiT_{46}(OT_{47})(OT_{48})$, $SiT_{46}T_{47}(OT_{48})$; or a radical —XS;

$L_1$, $L_2$ or $L_3$ independently of each other are hydrogen, C1-C22 alkyl; C2-C22 alkenyl, C2-C22 alkinyl; C3-C12 cycloalkyl; C3-C12 cycloalkenyl; C7-C20 aralkyl; C1-C20 heteroalkyl; C3-C12 cycloheteroalkyl; C5-C11 heteroaralkyl; C6-C20 aryl, C4-C9 heteroaryl; CN; OH; —$OT_{43}$; or —$COOT_{43}$;

$T_{43}$ is hydrogen; C1-C22 alkyl; C2-C22 alkenyl; C2-C22 alkinyl; C3-C12 cycloalkyl; C3-C12 cycloalkenyl; C7-C20 aralkyl; C1-C20 heteroalkyl; C3-C12 cycloheteroalkyl; C5-C11 heteroaralkyl; C6-C20 aryl; or C4-C9 heteroaryl;

$L_1$ and $L_2$, $L_1$ and $L_3$, $L_2$ and $L_3$, $L_1$ and $T_{38}$, $L_2$ and $T_{38}$, $L_1$ and $T_{35}$, $L_2$ and $T_{35}$, $L_3$ and $T_{35}$, $L_3$ and $T_{39}$, $T_{37}$ and $T_{38}$, $T_{35}$ and $T_{36}$, $T_{41}$ and $T_{42}$, $T_{39}$ and $T_{40}$ may be linked together to form 1, 2, 3 or 4 carbocyclic or N, O and/or S-heterocyclic rings, which may be further fused with other aromatic rings;

$T_{44}$, $T_{45}$, $T_{46}$, $T_{47}$, $T_{48}$, $T_{49}$, $T_{50}$ independently of each other are C1-C22alkyl; C3-C12 cycloalkyl; C2-C12 alkenyl; C3-C12 cycloalkenyl; C6-C14 aryl; C4-C12 heteroaryl; C7-C18 aralkyl or C5-C16 heteroaralkyl;

or $T_{44}$ and $T_{45}$, $T_{46}$ and $T_{47}$, $T_{47}$ and $T_{48}$ and/or $T_{49}$ and $T_{50}$ may be linked together to form unsubstituted or with C1-C4 alkyl substituted pyrrolidine, piperidine, piperazine or morpholine;

X represents a linker;

S signifies a silane-, oligosiloxane- or polysiloxane-moiety, q=1 or integer, preferred 1 to 6.

These compounds are described in WO 2009/027258 (expressly incorporated by reference).

The micronized preferably insoluble organic screening agent(s) according to the invention are generally present in the screening compositions according to the invention at a total concentration ranging from 0.1% and 15% by weight approximately, and preferably from 0.2% and 10% by weight approximately, relative to the total weight of the composition.

The insoluble organic screening agents according to the invention are provided in micronized form. The mean or average size of the particles (as defined above) ranges from 0.01 µm to 2 µm and more preferably from 0.02 µm to 1.5 µm and even more preferably from 0.03 µm to 1.0µm.

The preferably insoluble organic screening agents according to the invention may be provided in the desired particulate form by any appropriate means such as, in particular, grinding in the dry state or in solvent medium, sieving, spray-drying, micronization or spraying.

The preferably insoluble organic screening agents according to the invention in micronized form may, in particular, be provided by a method of grinding an insoluble UV-screening agent in the form of particles having a coarse size in the presence of an appropriate surfactant which makes it possible to enhance the dispersion of the particles thus obtained in the cosmetic formulations.

One embodiment of a method of micronization of insoluble organic screening agents is described in GB-A-2,303,549 and EP-A-893119 incorporated by reference herein. The grinding apparatus according to the invention may be a jet mill, a ball mill, a vibratory mill or a hammer mill and preferably a mill featuring high-speed agitation or an impact mill and more particularly a rotating ball mill, a vibratory mill, a tube mill or a rod mill.

According to this particular methodology, the alkyl polyglucosides having the structure $C_nH_{2n+1}O(C_6H_{10}O_5)_xH$ in which n is an integer from 8 to 16 and x is the average degree of polymerization of the structural unit $(C_6H_{10}O_5)$ and ranges from 1.4 to 1.6, are included as surfactants for the grinding of the screening agents. They are advantageously selected from among C1-C12 esters of a compound having the structure $C_nH_{2n+1}O(C_6H_{10}O_5)_xH$ and more precisely an ester prepared by reacting a C1-C12 carboxylic acid such as formic, acetic, propionic, butyric, sulfosuccinic, citric or tartaric acid with one or more free OH functions on the glucoside unit $(C_6H_{10}O_5)$. Such surfactants are typically employed at a concentration ranging from 1% to 50% by weight and more preferably from 5% to 40% by weight relative to the insoluble screening agent in its micronized form.

The UV-photo-protecting cosmetic composition according to the invention may of course contain one or more additional organic screening agents which are active in UV-A and/or UV-B ranges (absorbers), which are soluble in at least one of the phases of the subject compositions. These additional screening agents may be selected, in particular, from among the cinnamic derivatives; the dibenzoylmethane derivatives; the salicylic derivatives, the camphor derivatives; the triazine derivatives such as those described in U.S. Pat. No. 4,367,390, EP-0,863,145, EP-0,517,104, EP-0,570,838, EP-0,796,851, EP-0,775,698, EP-0,878,469 and EP-0,933,376; the benzophenone derivatives; the dimers derived from [alpha]-alkylstyrene such as those described in DE-198,55,649; the [beta], [beta]'-diphenylacrylate derivatives; the benzimidazole derivatives; the bisbenzoazolyl derivatives as described in EP-A-0,669,323 and U.S. Pat. No. 2,463,264; the p-aminobenzoic acid derivatives; the polymer screening agents and silicone screening agents such as those described, in particular, in WO-93/04,665.

Examples of such additional sunscreening agents active in the UV-A and/or UV-B ranges, which are soluble in at least one of the phases of the subject compositions, include:

p-aminobenzoic acid;
oxyethylenated p-aminobenzoate (25 mol);
2-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyl-dibenzoylmethane;
2-ethyl hexyl 4-methoxycinnamate;
methyl diisopropylcinnamate;
isoamyl 4-methoxycinnamate;
diethanolamine 4-methoxycinnamate;
menthyl anthranilate;
2-ethylhexyl-2-cyano-3,3'diphenylacrylate;
ethyl 2-cyano-3,3'-diphenylacrylate;
2-phenylbenzimidazole-5-sulfonic acid and salts thereof;
3-(4'-trimethylammonium)benzylidenebornan-2-one methyl sulfate;
2-hydroxy-4-methoxybenzophenone;
2-hydroxy-4-methoxybenzophenone-5-sulfonate;
2,4-dihydroxybenzophenone;
2,2'-4,4'-tetrahydroxybenzophenone;
2,2'-dihydroxy-4,4'-dimethoxybenzophenone;
2-hydroxy-4-n-octoxybenzophenone;
2-hydroxy-4-methoxy-4'-methyl benzophenone;
alpha-(2-oxoborn-3-ylidene)tolyl-4-sulfonic acid and its soluble salts;
3-(4'-sulfo)benzylidenebornan-2-one and its soluble salts;
3-(4'-methylbenzylidene)-d,l-camphor;
3-benzylidene-d,l-camphor;
1,4-benzene[di(3-methylidene-10-camphorsulfonic)] acid and its soluble salts;
urocanic acid;
2,4-bis{[4-2-ethylhexyloxy)]-2-hydroxy]phenyl}-6-(4-methoxyphenyl)-1,3,5-triazine; the polymer of N-(2- and 4)-[(2-oxoborn-3-ylidene)methyl]benzyl]acrylamide;
1,4-bisbenzimidazolylphenylene-3,3',5,5'-tetrasulfonic acid and its soluble salts;
polyorganosiloxanes containing a benzalmalonate function;
polyorganosiloxanes containing a benzotriazole function such as drometrizole trisiloxane.

The compositions according to the invention may also contain agents for tanning and/or for artificial tanning of the skin (self-tanning agents), such as, for example, dihydroxyacetone (DHA).

The cosmetic compositions according to the invention may also contain pigments or, alternatively, nanopigments (mean size of the primary particles: generally ranging from 5 nm to 100 nm, preferably from 10 nm to 50 nm) of metal oxides, coated or uncoated, such as, for example, nanopigments of titanium dioxide (amorphous or crystallized in the rutile and/or anatase state), of iron oxide, zinc oxide, zirconium oxide or cerium oxide, which are all UV photoprotective agents well known per se. Conventional coating agents are moreover alumina and/or aluminum stearate. Such nanopigments of metal oxides, coated or uncoated, are, in particular, described in EP-A-0,518,772 and EP-A-0,518,773.

The compositions of the invention may comprise, in addition, conventional cosmetic additives and adjuvants (collectively designated as auxiliaries) selected, in particular, from among fatty substances, organic solvents, thickeners, demulcents, opacifiers, colorants, stabilizers, emollients, antifoaming agents, moisturizing agents, perfumes, preservatives, polymers, fillers, sequestrants, propellants, alkalinizing or acidifying agents or any other ingredient customarily formulated into cosmetics, in particular for the production of anti-sun/sunscreen compositions in the form of emulsions.

The fatty phase (b) forming substances may be an oil or a wax or mixtures thereof, and they also comprise fatty acids, fatty alcohols and esters of fatty acids (all with at least 8 carbon atoms, preferably at least 10 carbon atoms). The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents include the lower alcohols and polyols.

The compositions of the invention may be formulated according to techniques well known to this art, in particular those suited for the preparation of emulsions of the water-in-oil type.

The subject compositions may be provided, in particular, in the form of a simple or complex (O/W/O or W/O/W) emulsion such as a cream, a milk, a gel or a gel cream, of a powder, a lotion, an ointment, a solid stick and may optionally be packaged as an aerosol and provided in the form of a foam, mousse or spray.

When an emulsion is provided, the aqueous phase thereof may comprise a nonionic vesicular dispersion prepared according to known techniques (Bangham, Standish and Watkins, J. Mol. Biol., 13, 238 (1965), FR-2,315,991 and FR-2,416,008).

The cosmetic compositions according to the invention may be formulated for protecting the human epidermis or the hair against the damaging effects of ultraviolet radiation, as an anti-sun composition or as a makeup product.

When the cosmetic compositions according to the invention are formulated for protecting the human epidermis against UV rays, or as anti-sun/sunscreen compositions, same may be provided in the form of a suspension or a dispersion in solvents or fatty substances, in the form of a nonionic vesicular dispersion or, alternatively, in the form of an emulsion, such as a cream or a milk, in the form of an ointment, a gel, a gel cream, a solid stick, a powder, a stick, an aerosol foam or a spray.

When the cosmetic compositions according to the invention are formulated for protecting the hair against UV rays, same may be provided in the form of a shampoo, a lotion, a gel, an emulsion, a nonionic vesicular dispersion and may constitute, for example, a rinse-off composition to be applied before or after shampooing, before or after dyeing or bleaching, before, during or after permanent-waving or hair straightening, a hair-styling or treatment lotion or gel, a lotion or gel for blow drying or hair setting, a composition for permanent waving or straightening, dyeing or bleaching the hair.

When the subject compositions are formulated as makeup products for the eyelashes, the eyebrows or the skin, such as a treatment cream for the epidermis, foundation, lipstick, eye-shadow, blusher, mascara or eyeliner, same may be provided in a solid or pasty, anhydrous or aqueous form, nonionic vesicular dispersions or alternatively suspensions.

As indicated above, the present invention thus features formulating the subject emulsions for the production of cosmetic compositions for protecting the skin and/or the hair against ultraviolet radiation, in particular solar radiation.

This invention also features formulating non-UV-screening organomodified silicones as described above for the production of photo-protective cosmetic or dermatological water-in-oil emulsions containing at least one organic UV-screening agent insoluble therein, for increasing the water resistance of its screening power (stability to water).

In order to further illustrate the present invention and the advantages thereof, the following specific formulation example is given, it being understood that same is intended only as illustrative and in nowise limitative.

A particularly preferred UV-photo-protecting cosmetic composition according to the invention, comprises:
3-40% by weight of the at least one fatty phase (b),
0.1 to 15% by weight of at least one micronized organic UV-screening agent (c), the mean particle size of said micronized particles ranging from 0.01 to 2 µm,
0.1 to 5% by weight at least one organomodified silicone (d) which does not comprise poly(oxyalkylene) moieties (d),
0 to 50% by weight of one or more auxiliary substances,
water as aqueous phase (a) adds up to 100% by weight.

Exemplarily the UV-photo-protecting cosmetic composition according to invention is prepared by a process where at least one emulsifier is blended with at least one fatty phase ingredient b), at least one organomodified silicone which does not comprise poly(oxyalkylene) moieties d) and at least micronized organic UV-screening agent c), and optionally further auxiliaries to form a fatty phase A). Then an aqueous phase B) comprising water and optionally polar organic solvents like alcohol, for example, polyols like glycerol, and optionally salts like NaCl, is provided. Then fatty phase A) is homogenized with a mixer and aqueous phase B) is slowly added thereto.

In another preferred embodiment, the at least micronized organic UV-screening agent c) optionally together with zinc oxide as phase C) is added as a separate phase to phase A), where after aqueous phase B) is added thereto.

EXAMPLE 1

Synthesis of an emulsifier containing stearic acid ester moieties and N-methylglucamine moieties 164.93 g (0.012 mol) of an epoxy modified silicone of the structure

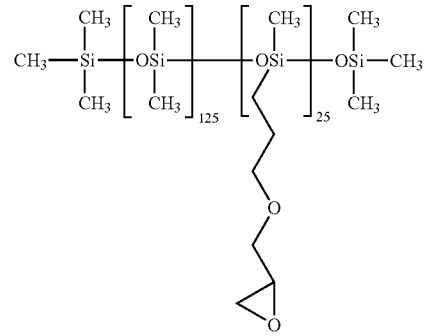

85.07 g (0.299 mol) stearic acid, 1.25 g triethylamine and 107 g propylene glycol mono methyl ether are mixed at room temperature and heated to reflux for 10 hours. The epoxide conversion at this point of the reaction is 97.1% (determined by means of 1H-NMR).

5.84 g (0.0299 mol) N-methylglucamine are added and the reaction mixture maintained at reflux for additional 4 hours. The epoxide conversion at this point of the reaction is 100% (determined by means of 1H-NMR).

The solvent is removed at 70° C. /20mbar. A yellow to slightly brownish wax like material melting at approx. 35° C. is obtained in quantitative yield.

97.5 g of the polymer+2.5 g 1.2-butylene glycol are mixed yielding an at room temperature low viscous and easily dispersable wax (=emulsifier blend 1).

EXAMPLE 2

Synthesis of an emulsifier containing stearic acid ester moieties, oleic acid ester moieties and N-methylglucamine moieties 165.03 g (0.012 mol) of an epoxy modified silicone of the structure

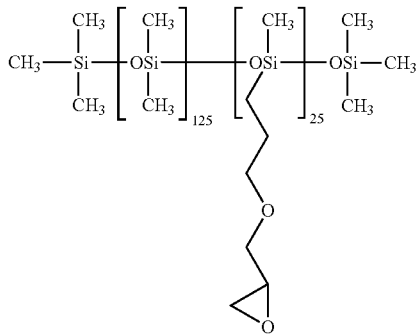

64.69 g (0.2274 mol) stearic acid, 20.28 g (0.0718 mol) oleic acid, 1.25 g triethylamine and 107 g propylene glycol mono methyl ether are mixed at room temperature and heated to reflux for 10 hours. The epoxide conversion at this point of the reaction is 98.2% (determined by means of 1H-NMR).

5.84 g (0.0299 mol) N-methylglucamine are added and the reaction mixture maintained at reflux for additional 4 hours. The epoxide conversion at this point of the reaction is 100% (determined by means of 1H-NMR).

The solvent is removed at 70° C. /20mbar. A yellow viscous fluid solidifying at approx. 20° C. is obtained in quantitative yield.

97.5 g of the polymer+2.5 g 1.2-butylene glycol are mixed yielding an at room temperature slowly flowing liquid (= emulsifier blend 2).

EXAMPLE 3

Preparation of W/O emulsions containing the emulsifiers according to the invention Components (amounts given in g)

EXAMPLE 3.1

| Components (amounts given in g) | Example 3.1 |
|---|---|
| Phase A | |
| Emulsifier blend 2 | 2 |
| PDMS 5 mPas (M5 Momentive Performance Materials) | 10 |
| Caprylic/Capric Triglyceride (Miglyol 812 Sasol) | 4 |
| Dicaprylyl carbonate (Cognis) | 4 |

-continued

| Components (amounts given in g) | Example 3.1 |
|---|---|
| Cetearyl Methicone (SF 1632 Momentive Performance Materials) | 2 |
| 3,3,5 Trimethylcyclohexyl salicylate (Eusolex HMS Merck) | 8 |
| Ethylhexyl salicylate (Neoheliopan OS, Haarmann & Reimer) | 3 |
| Butyl methoxydibenzoyl methane (Escalol 517, ISP Van Dyk) | 2 |
| Bis-ethylhexyloxyphenol-methoxyphenyl-triazine (Tinosorb S CIBA/BASF) | 2 |
| Phase B | |
| Water | 60 |
| Glycerol | 2 |
| NaCl | 1 |

Phase A is homogenized at 50° C. with a mixer, Phase B added slowly.

EXAMPLE 4

Preparation of W/O emulsions containing the emulsifiers according to the invention Components (amounts given in g)

| Components (amounts given in g) | Example 4.1 |
|---|---|
| Phase A | |
| Cyclomethicone + Trimethylsiloxysilicate (SS 4230 Momentive Performance Materials) | 1.9 |
| D5 (SF1202 Momentive Performance Materials) | 12 |
| Caprylyl Methicone (Silsoft 034 Momentive Performance Materials) | 5.6 |
| Emulsifier blend 1 | 1 |
| Ethylhexyl methoxy cynnamate (Neo Heliopan AV Haarmann & Reimer)) | 3.7 |
| Cetearyl Methicone (SF 1632 Momentive Performance Materials) | 2 |
| Phase B | |
| Bis-ethylhexyloxyphenol-methoxyphenyl-triazine (Tinosorb S CIBA/BASF) | 3.5 |
| Zinc oxide transparent (Lanxess) | 7 |
| Phase C | |
| water | 60.2 |
| ethanol | 2.5 |
| NaCl | 0.6 |

Phase A is homogenized at 50° C. with a mixer, Phase B added slowly and finallyPhase C added dropwise.

For both examples 3.1 and 4.1 stable, white, creamy and paste like W/O formulations are obtained.

The invention claimed is:

1. An UV-photo-protecting cosmetic composition, comprising:
   (a) at least one aqueous phase,
   (b) at least one fatty phase,
   (c) at least one micronized organic UV-screening agent, the mean particle size of said micronized particles ranging from 0.01 to 2 μm, and
   (d) at least one organomodified silicone which does not comprise poly(oxyalkylene) moieties, wherein
   said at least one organomodified silicone has the following structural formula (I):

$$[M_a D_b T_c Q_d]_e \qquad (I)$$

wherein
M=R$_3$SiO$_{1/2}$,
D=R$_2$SiO$_{2/2}$,
T=RSiO$_{3/2}$,
Q=SiO$_{4/2}$,
with
a=1-10
b=0-1000
c=0-1
d=0-1
e=1-10
wherein R=C$_1$ to C$_{22}$-alkyl, fluoro-substituted C$_1$ to C$_{22}$-alkyl, C$_2$ to C$_{22}$-alkylene, or C$_6$ to C$_{20}$ aryl, which is bound to Si via a carbon atom,
with the requirement that at least one group R is replaced by at least one group R$^{11}$ and at least one group R$^{12}$, wherein
R$^{11}$=—Z-(E)$_y$, wherein
E is
  E$^{21}$=—NR$^4$R$^5$,
    wherein R$^4$ and R$^5$ identical or different, selected from the group consisting of: hydrogen and straight chained, cyclic or branched, saturated or unsaturated C1 to C9 hydrocarbon radicals, optionally containing one or more groups selected from —O—, —NH—, —NR$^3$—, wherein R$^3$ =straight chained, cyclic or branched, saturated or unsaturated hydrocarbon radical with up to 6 carbon atoms, and —C(=O)—, and wherein the straight chained, cyclic or branched, saturated or unsaturated C1 to C9 hydrocarbon radicals are optionally substituted by one or more OH— and/or —NH$_2$ groups, and
E optionally comprises
  E$^{11}$=—O—C(=O)—R$^{21}$,
    wherein R$^{21}$ = straight chained, cyclic or branched, saturated or unsaturated C1 to C6 hydrocarbon radicals, optionally containing one or more groups selected from —O—, —NH—, —NR$^3$—, —C(=O)—, and wherein the straight chained, cyclic or branched, saturated or unsaturated C1 to C6 hydrocarbon radicals are substituted by one or more OH-groups, wherein R$^3$ = straight chained, cyclic or branched, saturated or unsaturated hydrocarbon radical with up to 6 carbon atoms, and
R$^{12}$ =—Z-(E)$_y$, wherein
  E =E$^{12}$ =—O—C(=O)—R$^{22}$, wherein
    R$^{22}$ = straight chained, cyclic or branched, saturated or unsaturated C7 to C22 hydrocarbon radical, optionally containing one or more groups selected from —O—, —NH—, —NR$^3$—, wherein R$^3$ is as defined above, and —C(=O)—, and wherein straight chained, cyclic or branched, saturated or unsaturated C7 to C22 hydrocarbon radical is also optionally substituted by one or more OH-groups,
Z =a bivalent or trivalent straight-chained, cyclic or branched, saturated or unsaturated C2 to C20 hydrocarbon residue,
wherein Z optionally further comprises one or more groups selected from
*—O—**, *—NH—** and

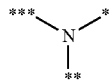

wherein * and  and * denote bonds to different carbons in the C2 to C20 hydrocarbon residue, and wherein Z is substituted by one or more —OH groups, or
wherein Z is a bivalent or trivalent straight-chained, cyclic or branched, saturated or unsaturated C2 to C20 hydrocarbon residue, and
y=1 or 2.

2. The UV-photo-protecting cosmetic composition of claim 1, wherein the group Z comprises at least one residue selected from the group consisting of:
—(CH$_2$)$_z$—wherein z is 1 to 10,

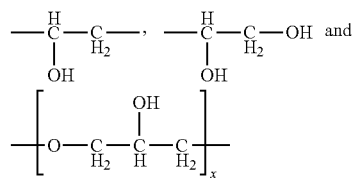

wherein x =1 -4.

3. The UV-photo-protecting cosmetic composition of claim 1, wherein the group Z is a residue selected from the group of the formulas:

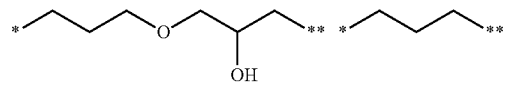

wherein * denotes the bond to the silicon atom and ** denotes the bond to the residue E.

4. The UV-photo-protecting cosmetic composition of claim 1, wherein the at least one organomodified silicone (d) comprises structural elements selected from the following formulas:

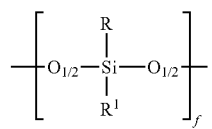

wherein f=0-600,

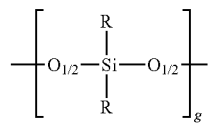

wherein g=0-700,

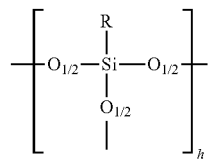

wherein h=0-10,
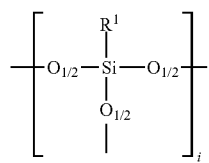
wherein i=0-10,
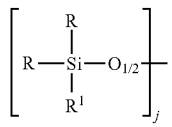
wherein j=0-30,
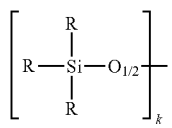
wherein k=0-30,
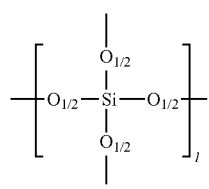
wherein l=0-10, and wherein f+g+h+i+j+k+l=12 to 1000.
5. The UV-photo-protecting cosmetic composition of claim 1, wherein the residues $R^{11}$ are selected from the group consisting of:
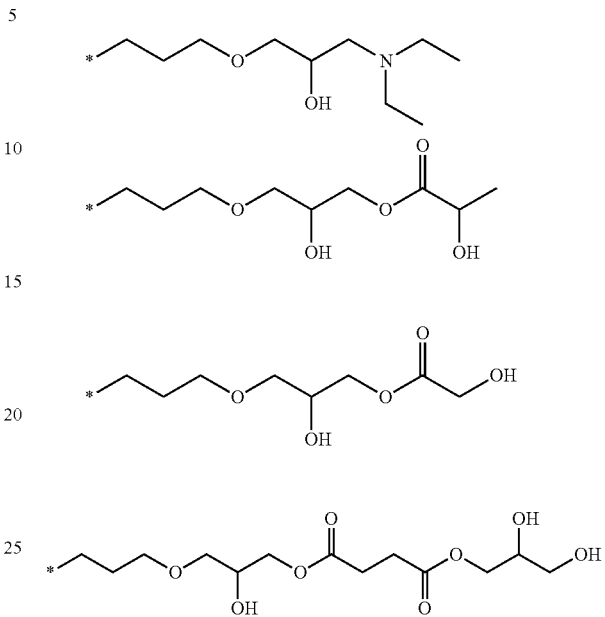
and
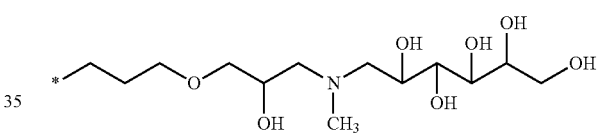
and wherein the residues $R^{12}$ are selected from the group consisting of:
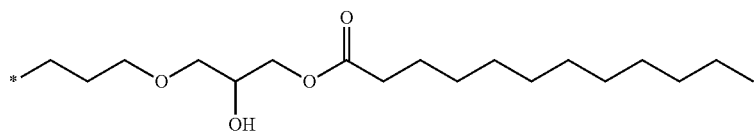
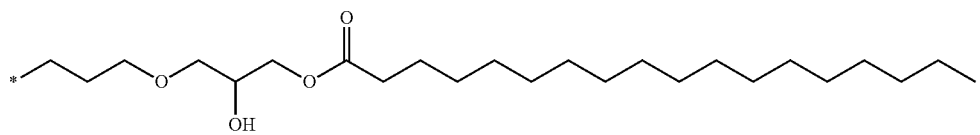
and
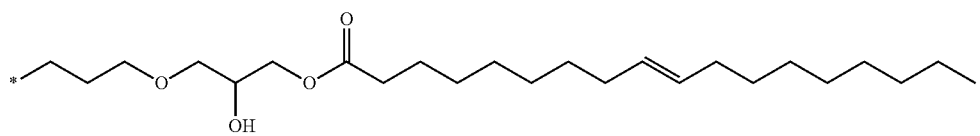

6. The UV-photo-protecting cosmetic composition of claim 1, wherein the least one organomodified silicone free of poly(oxyalkylene) moieties is present in an amount of from 0.1% to 20% by weight.

7. The UV-photo-protecting cosmetic composition of claim 1, wherein the micronized organic UV-screening agent is selected from the group consisting of an oxanilide, a triazine, a triazole, a vinylamide, a cinnamide, and combinations thereof.

8. The UV-photo-protecting cosmetic composition of claim 1, wherein the micronized organic UV-screening agent is a triazine-based UV-screening agent.

9. The UV-photo-protecting cosmetic composition of claim 1, wherein the fatty phase comprises synthetic or natural oils or fats.

10. The UV-photo-protecting cosmetic composition of claim 1, wherein:
   the at least one fatty phase (b) is present in an amount of 3-40% by weight,
   the at least one micronized organic UV-screening agent (c) is present in an amount of 0.1 to 15% by weight, wherein the mean particle size of said micronized particles is from 0.01 to 2μm,
   the at least one organomodified silicone (d) which does not comprise poly(oxyalkylene) moieties is present in an amount of 0.1 to 5% by weight, and
   the composition further comprises 0 to 50% by weight of at least one auxiliary substance, and
   sufficient water to bring the total formulation up to 100% by weight.

11. The UV-photo-protecting cosmetic composition of claim 1, formulated as at least one of a cream, a milk, a gel, a lotion, an ointment, a gel cream, a suspension, a dispersion, a powder, a shampoo, a solid stick, a foam and a spray.

12. The UV-photo-protecting cosmetic composition of claim 2, formulated as at least one of a cream, a milk, a gel, a lotion, an ointment, a gel cream, a suspension, a dispersion, a powder, a shampoo, a solid stick, a foam and a spray.

13. The UV-photo-protecting cosmetic composition of claim 3, formulated as at least one of a cream, a milk, a gel, a lotion, an ointment, a gel cream, a suspension, a dispersion, a powder, a shampoo, a solid stick, a foam and a spray.

14. The UV-photo-protecting cosmetic composition of claim 4, formulated as at least one of a cream, a milk, a gel, a lotion, an ointment, a gel cream, a suspension, a dispersion, a powder, a shampoo, a solid stick, a foam and a spray.

15. The UV-photo-protecting cosmetic composition of claim 5, formulated as at least one of a cream, a milk, a gel, a lotion, an ointment, a gel cream, a suspension, a dispersion, a powder, a shampoo, a solid stick, a foam and a spray.

16. The UV-photo-protecting cosmetic composition of claim 5, wherein
   the residues $R^{11}$ are hydrophilic and have a logP (25° C.) of <0.5 and
   the residues $R^{12}$ are lipophilic and have a logP (25° C.) of ≥0.5,
   the logP values determined on the basis of the corresponding compounds $H-R^{11}$ and $H-R^{12}$.

17. The UV-photo-protecting cosmetic composition of claim 1, wherein the residues $R^{11}$ comprise:

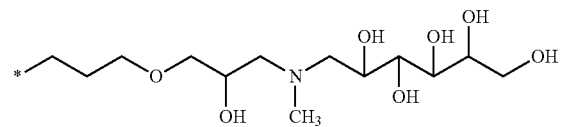 [SMILES: *CCCOCC(O)CN(C)CC(O)C(O)C(O)C(O)CO]

and optionally comprise
$E^{11}-O-C(=O)-R^{21}$
   wherein $R^{21}$ =straight chained, cyclic or branched, saturated or unsaturated C1 to C6 hydrocarbon radical, optionally containing one or more groups selected from $-O-$, $-NH-$, $-NR^3-$, $-C(=O)-$, and substituted by one or more OH-Groups, wherein $R^3$ =straight chained, cyclic or branched, saturated or unsaturated hydrocarbon radical with up to 6 carbon atoms.

* * * * *